(12) United States Patent
Jana et al.

(10) Patent No.: US 11,981,774 B2
(45) Date of Patent: May 14, 2024

(54) CROSSLINKED POLYMER AND RELATED METHODS THEREOF

(71) Applicant: AGENCY FOR SCIENCE, TECHNOLOGY AND RESEARCH, Singapore (SG)

(72) Inventors: Satyasankar Jana, Singapore (SG); Jayasree Seayad, Singapore (SG); Abdul Majeed Seayad, Singapore (SG); Ping Sen Choong, Singapore (SG)

(73) Assignee: AGENCY FOR SCIENCE, TECHNOLOGY AND RESEARCH, Singapore (SG)

( * ) Notice: Subject to any disclaimer, the term of this patent is extended or adjusted under 35 U.S.C. 154(b) by 542 days.

(21) Appl. No.: 17/043,448

(22) PCT Filed: Mar. 29, 2019

(86) PCT No.: PCT/SG2019/050183
§ 371 (c)(1),
(2) Date: Sep. 29, 2020

(87) PCT Pub. No.: WO2019/190408
PCT Pub. Date: Oct. 3, 2019

(65) Prior Publication Data
US 2021/0024698 A1    Jan. 28, 2021

(30) Foreign Application Priority Data

Mar. 29, 2018 (SG) .............................. 10201802688T
Mar. 29, 2018 (SG) ............................ 10201802689R

(51) Int. Cl.
| | | |
|---|---|---|
| C08G 71/04 | (2006.01) |
| C07D 405/14 | (2006.01) |
| C07D 407/14 | (2006.01) |
| C08F 283/00 | (2006.01) |
| C09D 175/12 | (2006.01) |

(52) U.S. Cl.
CPC ........... C08G 71/04 (2013.01); C07D 405/14 (2013.01); C07D 407/14 (2013.01); C08F 283/00 (2013.01); C09D 175/12 (2013.01)

(58) Field of Classification Search
None
See application file for complete search history.

(56) References Cited

FOREIGN PATENT DOCUMENTS

JP    2022541406 A  *  7/2020

OTHER PUBLICATIONS

JP 2022541406 A English machine translation (Year: 2020).*
European Extended search report dated Dec. 2, 2021 for EP Application No. 19776531.6.
(Continued)

*Primary Examiner* — Jeffrey D Washville
(74) *Attorney, Agent, or Firm* — EIP US LLP; Jared A. Barnard

(57) ABSTRACT

There is provided a method of crosslinking a polyhydroxyurethane (PHU) polymer having a plurality of diene moieties, preferably furan in the backbone and a crosslinked PHU polymer by reacting with a crosslinking agent having two or more dienophile moieties. Also provided is a method of removing the crosslinks of a crosslinked PHU polymer comprising a plurality of diene-dienophile adducts.

19 Claims, 13 Drawing Sheets

(56) References Cited

OTHER PUBLICATIONS

Dolci et al., "Remendable thermosetting polymers for isocyanate-free adhesives: a preliminary study", Polymer Chemistry, vol. 6, No. 45, Jan. 1, 2015 (Jan. 1, 2015), pp. 7851-7861, XP055863321, ISSN: 1759-9954, DOI: 10.1039/C5PY01213A.

Karami et al., "Bio-based thermo-healable non-isocyanate polyurethane DA network in comparison with its epoxy counterpart", Journal of CO2 Utilization, vol. 18, Mar. 1, 2017 (Mar. 1, 2017), pp. 294-302, XP055863328, NL ISSN: 2212-9820, DOI: 10.1016/j.jcou.2017.02.009.

International Search Report and Written Opinion dated May 30, 2019 for PCT Application No. PCT/SG2019/050183.

Dolci, E. et al., "Thermoresponsive crosslinked isocyanate-free polyurethanes by Diels-Alder polymerization", Journal of Applied Polymer Science, Sep. 26, 2016, vol. 134, No. 5, p. 44408 (1-11), DOI: 10.1002/APP.44408.

Karateev, A. et al., "Nonisocyanate" Polyhydroxy Urethanes Based on the Raw Material of a Plant Origin, Chemistry & Chemical Technology, Dec. 31, 2014, vol. 8, No. 3, pp. 329-338, DOI: 10.23939/CHCHT08.03.329.

Zhang, L. et al., "A novel 2,5-furandicarboxylic acid-based bis(cyclic carbonate) for the synthesis of biobased nonisocyanate polyurethanes", RSC Advances, Dec. 22, 2016, vol. 7, No. 1, pp. 37-46, DOI: 10.1039/C6RA25045A.

Gu, L. et al., "Recyclable bio-based crosslinked polyurethanes with self-healing ability", Journal of Applied Polymer Science, Feb. 6, 2018, vol. 135, No. 21, p. 46272 (1-7), DOI: 10.1002/APP.46272.

Wei, Y. et al., "The self-healing cross-linked polyurethane by Diels-Alder polymerization", Advances in Polymer Technology, Jun. 19, 2017, vol. 37, No. 6, pp. 1987-1993, DOI: 10.1002/ADV.21857.

Lu, Y-L. et al., "Self-healing polymers based on thermally reversible Diels-Alder chemistry", Polymer Chemistry, Dec. 11, 2012, vol. 4, No. 7, pp. 2194-2205.

\* cited by examiner

Scheme 2. Synthesis of crosslinked PHUs/NIPUs from bio-originated monomers

CROSSLINKED POLYMER AND RELATED METHODS THEREOF

CROSS-REFERENCE TO RELATED APPLICATIONS

This application is a 371 of International Application No. PCT/SG2019/050183, filed Mar. 29, 2019, which claims priority to Singapore Application No. 10201802688T, filed Mar. 29, 2018 and 10201802689R filed Mar. 29, 2018, under 35 U.S.C. § 119(a). Each of the above-referenced patent applications is incorporated by reference in its entirety.

TECHNICAL FIELD

Various embodiments disclosed herein relate broadly to a method of crosslinking a polymer, a crosslinked polymer and a method of removing the crosslinks of said crosslinked polymer.

BACKGROUND

Polyurethanes (PUs) are one of the most versatile classes of polymeric materials having many outstanding properties. They can be used in several applications such as in the manufacture of coatings, foams (rigid and soft), adhesives, sealants and fibers etc.

Traditional polyurethanes (PUs) are synthesized by the reaction of di-functional or poly-functional hydroxyl compounds (—R—(OH)$_n$) with di-functional or poly-functional isocyanate compounds (—R—(N=C=O)$_n$), usually in the presence of a catalyst. However, such currently used production methods are faced with several drawbacks.

Firstly, isocyanates are moisture sensitive. These hydrolytically unstable isocyanate bonds that are present within the polyurethene polymer makes the polymer vulnerable to environmental degradation.

Next, isocyanates and their predecessor compound, i.e. phosgene are highly toxic compounds and are considered chemical irritants. Isocyanates have also been classified as potential human carcinogens. Using such toxic components in the current methods of synthesizing polyurethanes is dangerous as they are hazardous to human health and also detrimental to the environment. As exposure to these toxic components can cause adverse health effects, the cost of production for such methods are high as implementation of safety measures and protocols are necessary to protect workers during the manufacturing process. New governmental regulations to limit the use of toxic chemicals also compound to the challenges faced by traditional methods of PU synthesis.

In view of the above, there is thus a need to address or at least ameliorate one of the problems described above.

SUMMARY

In one aspect, there is provided a method of crosslinking a polyhydroxyurethane (PHU) or non-isocyanate polyurethane (NIPU) polymer having a plurality of diene moieties in the backbone, the method comprising:
reacting a crosslinking agent having two or more dienophile moieties with the PHU polymer backbone to form crosslinks between the diene moieties.

In one embodiment, the crosslinking occurs below a threshold temperature beyond which crosslinks are removed from the PHU polymer.

In one embodiment, the crosslinking is carried out at ambient room temperature.

In one embodiment, the diene moiety comprises a furan moiety.

In one embodiment, the dienophile moiety comprises a maleimide moiety.

In one embodiment, the crosslinking agent is a bismaleimide.

In one embodiment, the bismaleimide is selected from the group consisting of 1,1'-(Methylenedi-4,1-phenylene)bismaleimide (BM1), N,N'-hexamethylenebismaleimide, (BM2), N,N'-(1,4-Phenylene)dimaleimide (BM3) and N,N'-pentamethylenebismaleimide (BM4).

In one embodiment, the PHU polymer and the crosslinking agent are reacted in a molar ratio of 1:0.05-1.

In one embodiment, the method further comprises reacting at least one biscarbonate with at least one amine containing compound to form the PHU polymer, prior to reacting the PHU polymer with the crosslinking agent, wherein at least one of the biscarbonate or amine containing compound comprises a diene moiety.

In one embodiment, the biscarbonate is selected from the group consisting of sebacate bis-carbonate (SBC), terephthalic bis-carbonate (TBC), benzene bis-carbonate (BBC), methyl bis-carbonate (MBC), succinic bis-carbonate (SuBC), bis((2-oxo-1,3-dioxolan-4-yl)methyl)furan-2,5-dicarboxylate (FBC1), 4,4'-(((furan-2,5-diylbis(methylene))bis(oxy))bis(methylene))bis(1,3-dioxolan-2-one) (FBC2), bis((2-oxo-1,3-dioxolan-4-yl)methyl)pyridine-2,5-dicarboxylate (PBC), bis((2-oxo-1,3-dioxolan-4-yl)methyl)pyridine-2,6-dicarboxylate (PBC-2) and 4,4'-(((tetrahydrofuran-3,4-diyl)bis(oxy))bis(methylene))bis(1,3-dioxolan-2-one) (HFBC), and the amine containing compound is selected from the group consisting of furan bis-amine (FBA), xylene diamine (XDA), diaminopentane (DAP) and hexamethylenediamine (HDA).

In one embodiment, the biscarbonate is prepared from a bio-based source.

In one embodiment, the amine containing compound is prepared from a bio-based source.

In one embodiment, the method further comprises functionalizing the PHU polymer with one or more substituents selected from the group consisting of alkyl, sulfate, sulfonate, phosphate, carboxylate, sulfobetaine, phosphobetaine, cinnamate, fatty acid, amino acid, lactic acid, polylactic acid, caprolactone, polycaprolactone, polysiloxane and combinations thereof to form a functionalized PHU polymer, prior to reacting said PHU polymer with the crosslinking agent.

In one aspect, there is provided a crosslinked polyhydroxyurethane (PHU) polymer obtained from the method as disclosed herein, the crosslinked polymer comprising a plurality of diene-dienophile adducts.

In one embodiment, the diene-dienophile adduct comprises a ring structure formed from a Diels-Alder reaction between the diene moiety and the dienophile moiety.

In one embodiment, at least a part of the Diels-Alder adduct comprises structure (I):

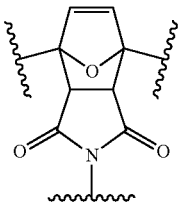

Structure (I)

In one embodiment, the crosslinked polymer is devoid of an isocyanate group.

In one embodiment, the diene moiety comprises furan.

In one embodiment, the dienophile moiety comprises maleimide.

In one embodiment, the maleimide is a bismaleimide represented by general formula (I):

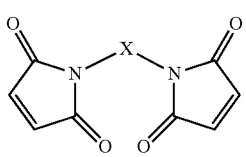

(I)

wherein X is a single bond, $C_1$-$C_{14}$ alkylene, polyethyleneglycol (PEG) or segments thereof, polypropylene glycol (PPG) or segments thereof, phenylene, methylenebis(phenylene), sulfonylbis(phenylene), oxybis(phenylene) and combinations thereof.

In one embodiment, the maleimide is a bismaleimide selected from the group consisting of 1,1'-(Methylenedi-4,1-phenylene)bismaleimide (BM1), N,N'-hexamethylenebismaleimide, (BM2),N,N'-(1,4-Phenylene)dimaleimide (BM3) and N,N'-pentamethylenebismaleimide (BM4).

In one embodiment, the crosslinks are removable at a temperature of more than 50° C.

In one embodiment, the crosslinked polymer has one or more of the following properties: easily recyclable, self-healing, thermo-healing and shape memory.

In one aspect, there is provided a method of removing the crosslinks of a crosslinked polyhydroxyurethane (PHU) polymer comprising a plurality of diene-dienophile adducts, the method comprising:
heating the crosslinked PHU polymer at a temperature of from more than 50° C. to remove the crosslinks.

In one aspect, there is provided a coated substrate comprising:
a layer of crosslinked polyhydroxyurethane (PHU) polymer as disclosed herein applied over a surface of the substrate.

In one embodiment, the substrate is selected from the group consisting of wood, glass, metal, plastic and fabric and combinations thereof.

Definitions

The terms "diene" or "diene moiety" as used herein broadly refer to a compound that contains at least two double bonds. For example, such a compound may contain at least one conjugated diene moiety (i.e. two conjugated C=C bonds) that is reactive towards a dienophile to form a Diels-Alder adduct/[4+2] cycloaddition adduct.

The terms "dienophile" or "dienophile moiety" as used herein broadly refer to a compound that contains at least one double bond or triple bond. For example, such a compound may contain at least one alkene or alkyne moiety (i.e. C=C bond or C≡C bond) that is reactive towards a diene to form a Diels-Alder adduct/[4+2]cycloaddition adduct. In various embodiments, the alkene or alkyne moiety is electron-deficient.

The terms "crosslinked", "crosslink" and "crosslinking" or grammatical variations thereof as used herein broadly refer to the process of forming bonds between chains of a polymer. In various embodiments, the "crosslinks" are reversible crosslinks such that the crosslinks between the polymer chains are readily removed upon exposure to a stimulus such as heat.

The terms "bio-based", "bio-derived" or "bio-originated" as used herein broadly refers to the quality of being derived or being originated from living organisms or once-living organisms. Such living organisms may be animal or plants. Therefore, "bio-based source" includes, but is not limited to, a biofeedstock, a plant-based source or combinations thereof. Examples of "bio-based source" include, but are not limited to, biomass such as cellulose, hemicellulose, lignin, hexose, glucose, fructose, erythritol and amino acids.

The terms "coupled" or "connected" or grammatical variations thereof as used in this description are intended to cover both directly connected or connected through one or more intermediate means, unless otherwise stated. Accordingly, the term "coupling agent" as used herein is to be interpreted broadly to include, but is not limited to, an agent (that may act as the single or one of the many intermediate means) that couples two or more entities together permanently or temporarily. The entities may be organic or inorganic and the coupling means between the agent and the entities includes, but is not limited to physical, chemical or biological bonding/interaction.

The term "and/or", e.g., "X and/or Y" is understood to mean either "X and Y" or "X or Y" and should be taken to provide explicit support for both meanings or for either meaning.

Further, in the description herein, the word "substantially" whenever used is understood to include, but not restricted to, "entirely" or "completely" and the like. In addition, terms such as "comprising", "comprise", and the like whenever used, are intended to be non-restricting descriptive language in that they broadly include elements/components recited after such terms, in addition to other components not explicitly recited. For example, when "comprising" is used, reference to a "one" feature is also intended to be a reference to "at least one" of that feature. Terms such as "consisting", "consist", and the like, may in the appropriate context, be considered as a subset of terms such as "comprising", "comprise", and the like. Therefore, in embodiments disclosed herein using the terms such as "comprising", "comprise", and the like, it will be appreciated that these embodiments provide teaching for corresponding embodiments using terms such as "consisting", "consist", and the like.

Further, terms such as "about", "approximately" and the like whenever used, typically means a reasonable variation, for example a variation of +/−5% of the disclosed value, or a variance of 4% of the disclosed value, or a variance of 3% of the disclosed value, a variance of 2% of the disclosed value or a variance of 1% of the disclosed value.

Furthermore, in the description herein, certain values may be disclosed in a range. The values showing the end points of a range are intended to illustrate a preferred range. Whenever a range has been described, it is intended that the range covers and teaches all possible sub-ranges as well as individual numerical values within that range. That is, the end points of a range should not be interpreted as inflexible limitations. For example, a description of a range of 1% to 5% is intended to have specifically disclosed sub-ranges 1% to 2%, 1% to 3%, 1% to 4%, 2% to 3% etc., as well as individually, values within that range such as 1%, 2%, 3%, 4% and 5%. The intention of the above specific disclosure is applicable to any depth/breadth of a range.

Additionally, when describing some embodiments, the disclosure may have disclosed a method and/or process as a particular sequence of steps. However, unless otherwise required, it will be appreciated that the method or process should not be limited to the particular sequence of steps disclosed. Other sequences of steps may be possible. The particular order of the steps disclosed herein should not be construed as undue limitations. Unless otherwise required, a method and/or process disclosed herein should not be limited to the steps being carried out in the order written. The sequence of steps may be varied and still remain within the scope of the disclosure.

DESCRIPTION OF EMBODIMENTS

Exemplary, non-limiting embodiments of a method of crosslinking a polyhydroxyurethane (PHU) polymer having a plurality of diene moieties, a crosslinked polyhydroxyurethane (PHU) polymer obtained from said method, and a method of undoing or reversing or removing the crosslinks of said crosslinked polyhydroxyurethane (PHU) polymer are disclosed hereinafter.

It will be appreciated that polyhydroxyurethane (PHU) polymer may also be referred to as poly(hydroxyurethane) or poly(hydroxy urethane). In various embodiments, the PHU is a non-isocyanate polyurethane (NIPU).

In various embodiments, there is provided a method of crosslinking a polyhydroxyurethane (PHU) polymer having a plurality of diene moieties, the method comprising: reacting a crosslinking agent having two or more dienophile moieties with the PHU polymer to form the crosslinks between the diene moieties.

In various embodiments, there is at least one, at least two, at least three, at least four, at least five, at least six, at least seven, at least eight, at least nine or at least ten diene moieties in each repeating unit of the polyhydroxyurethane (PHU) polymer. In some embodiments, there is one diene moiety in each repeating unit of the polyhydroxyurethane (PHU) polymer, for example when the polymer is obtained from the polymerisation of (i) a furan containing biscarbonate (such as bis((2-oxo-1,3-dioxolan-4-yl)methyl)furan-2,5-dicarboxylate and 4,4'-(((furan-2,5-diylbis(methylene))-bis(oxy))bis(methylene))bis(1,3-dioxolan-2-one)) and a non-furan containing bisamine (such as xylene diamine, diaminopentane, hexamethylenediamine) or (ii) a non-furan containing biscarbonate (such as bis((2-oxo-1,3-dioxolan-4-yl)methyl)pyridine-2,5-dicarboxylate, bis((2-oxo-1,3-dioxolan-4-yl)methyl)pyridine-2,6-dicarboxylate and 4,4'-(((tetrahydrofuran-3,4-diyl)bis(oxy))bis(methylene))bis(1,3-dioxolan-2-one)) and a furan containing bisamine (such as furan bis-amine). In other embodiments, there is two diene moieties in each repeating unit of the polyhydroxyurethane (PHU) polymer, for example when the polymer is obtained from the polymerisation of a furan containing biscarbonate (such as bis((2-oxo-1,3-dioxolan-4-yl)methyl)furan-2,5-dicarboxylate and 4,4'-(((furan-2,5-diylbis(methylene))-bis(oxy))bis(methylene))bis(1,3-dioxolan-2-one)) and a furan containing bisamine (such as furan bis-amine). Advantageously, embodiments of the PHU polymer allow the polymer to have multiple sites for crosslinking to occur under the method disclosed herein.

In various embodiments, the crosslinking agent having two or more dienophile moieties comprises at least two, at least three, at least four, at least five, at least six, at least seven, at least eight, at least nine or at least ten dienophile moieties in said crosslinking agent. In some embodiments, the crosslinking agent has two dienophile moieties in each molecule of the crosslinking agent.

In various embodiments, the step of reacting the crosslinking agent with the PHU polymer and/or crosslinking occurs below a threshold temperature beyond which crosslinks are removed from the PHU polymer. The crosslinking agent may be free/unblocked crosslinking agent or blocked crosslinking agent.

In various embodiments where free or unblocked crosslinking agents are used, the step of reacting the crosslinking agent with the PHU polymer and/or crosslinking is performed at a temperature of not more than about 90° C., not more than about 85° C., not more than about 80° C., not more than about 75° C., not more than about 70° C., not more than about 65° C. or not more than about 60° C. In various embodiments, the temperature is from about 15° C. to about 90° C., from about 16° C. to about 89° C., from about 17° C. to about 88° C., from about 18° C. to about 87° C., from about 19° C. to about 86° C., from about 20° C. to about 85° C., from about 21° C. to about 84° C., from about 22° C. to about 83° C., from about 23° C. to about 82° C., from about 24° C. to about 81° C., from about 25° C. to about 80° C., from about 26° C. to about 79° C., from about 27° C. to about 78° C., from about 28° C. to about 77° C., from about 29° C. to about 76° C., from about 30° C. to about 75° C., from about 35° C. to about 70° C., from about 40° C. to about 65° C., from about 45° C. to about 60° C., or from about 50° C. to about 55° C. As may be appreciated, in various embodiments, the temperature is not more than about 90° C., above which there will not be crosslink(s) formed between the crosslinking agent and the polymer. Accordingly, in various embodiments where free or unblocked crosslinking agents are used, the threshold temperature is about 90° C.

In various embodiments where blocked crosslinking agents are used, the step of reacting the crosslinking agent with the PHU polymer and/or crosslinking may be performed at a temperature of not more than about 90° C. or may also be performed at a higher temperature (such as at a temperature of more than about 90° C.). As may be appreciated, in various embodiments where blocked crosslinking agents are used, application of heat may be required to release free/unblocked crosslinking agent from its blocked form, i.e. in a deblocking process in order for the crosslinking agent to react with the PHU polymer. In such embodiments, free/unblocked crosslinking agents are generated in-situ in the reaction mixture before forming crosslinks with the polymer. Accordingly, in various embodiments where blocked crosslinking agents are used, the threshold temperature is more than ambient temperature or more than about 90° C.

In various embodiments, the step of reacting the crosslinking agent with the PHU polymer and/or crosslinking is performed at ambient room temperature. In various embodiments, the step of reacting the crosslinking agent with the PHU polymer and/or crosslinking does not require heat. In various embodiments, the ambient temperature is from about 15° C. to about 30° C., from about 16° C. to about 29° C., from about 17° C. to about 28° C., from about 18° C. to about 27° C., from about 19° C. to about 26° C., from about 20° C. to about 25° C., from about 21° C. to about 24° C., or from about 22° C. to about 23° C.

In various embodiments, the crosslinking occurs at a temperature of not more than about 90° C., not more than about 85° C., not more than about 80° C., not more than about 75° C., not more than about 70° C., not more than about 65° C., not more than about 60° C., not more than about 55° C., not more than about 50° C., not more than about 45° C., not more than about 40° C., not more than about 35° C. or not more than about 30° C. As may be appreciated, in various embodiments, crosslinking is carried out at a temperature that is not more than the threshold temperature, above which there will not be crosslink(s) formed between the crosslinking agent and the polymer. In various embodiments, the crosslinking is carried out at ambient room temperature. In various embodiments, the crosslinking does not require heat.

In various embodiments, the step of reacting the crosslinking agent with the PHU polymer comprises mixing the crosslinking agent with the PHU polymer. In various embodiments, the reaction step comprises mixing the crosslinking agent with the PHU polymer for a time period of at least about 5 mins, at least about 10 mins, at least about 15 mins, at least about 20 mins, at least about 25 mins, at least about 30 mins, at least about 35 mins, at least about 40 mins, at least about 45 mins, at least about 50 mins, at least about 55 mins, at least about 1 hour, at least about 2 hours, at least about 3 hours, at least about 4 hours, at least about 5 hours, at least about 6 hours, at least about 7 hours, at least about 8 hours, at least about 9 hours, at least about 10 hours, at least about 11 hours, at least about 12 hours, at least about 13 hours, at least about 14 hours, at least about 15 hours, at least about 16 hours, at least about 17 hours, at least about 18 hours, at least about 19 hours, at least about hours, at least about 21 hours, at least about 22 hours, at least about 23 hours, at least about 24 hours, at least about 48 hours, at least about 72 hours, at least about 4 days, at least about 5 days, at least about 6 days or at least about 7 days. In some embodiments, when the step of reacting the crosslinking agent with the PHU polymer is performed under ambient conditions such as ambient temperature and ambient pressure, the mixture is mixed for a time period of about 12 hours (for e.g. overnight), about 1 day, about 2 days or about 3 days at room temperature. In other embodiments, when the step of reacting the crosslinking agent with the PHU polymer is performed at an elevated temperature of from about 30° C. to about 90° C., about 50° C. or about 60° C., the mixture is mixed for a shorter time period, for example for a time period of about 1 hour, i.e. crosslinking may be speeded up at an elevated temperature.

In various embodiments, the step of reacting the crosslinking agent with the PHU polymer comprises mixing the crosslinking agent and the PHU polymer in the presence of a solvent. Any suitable solvent that effectively serves as a medium to contain the other components of the mixture may be used in embodiments of the method disclosed herein. In various embodiments, the solvent is water. In various embodiments, the solvent is an organic solvent. The organic solvent may be selected from but is not limited to the group consisting of dimethylformamide (DMF), tetrahydrofuran (THF), dichloromethane (DCM), acetonitrile (ACN), dimethyl sulfoxide (DMSO), γ-valerolactone (GVL), propylene carbonate (PC), dimethylcarbonate (DMC), dioxane, dioxolane, diglyme, acetone, methyl ethyl ketone (MEK) and the like and combinations thereof.

In various embodiments therefore, the method disclosed herein provides an easy, fast and straightforward way of crosslinking a polyhydroxyurethane (PHU) polymer as the use of catalyst and/or harsh chemical treatments and/or complex techniques may be avoided.

In various embodiments, the method comprises reacting a crosslinking agent having two or more dienophile moieties with the PHU polymer to incorporate crosslinks between the diene moieties in the PHU polymer. In various embodiments, the crosslinks are generated from a plurality of Diels-Alder reactions, each reaction involving a diene moiety of the PHU polymer and a dienophile moiety of the crosslinking agent. In these embodiments, the Diels-Alder reaction is a [4+2]cycloaddition between a diene moiety of the PHU polymer and a dienophile moiety of the crosslinking agent. In various embodiments, each crosslink comprises a plurality of diene-dienophile adducts. In various embodiments, each crosslink comprises two diene-dienophile adducts linking a repeating unit to another repeating unit of the PHU polymer.

Referring to Scheme 1, there is shown a polyhydroxyurethane (PHU) polymer being crosslinked between sites at (i) A and C, (ii) B and D or at (iii) A and C as well as B and D.

In various embodiments, at each of the sites A, B, C and D, there is a diene moiety on the PHU polymer chain that forms a diene-dienophile adduct with a dienophile moiety of the crosslinking agent.

In various embodiments, sites A, B, C and D are each a diene-dienophile adduct. In various embodiments of the crosslinked PHU polymer, there is a crosslink comprising two diene-dienophile adducts at A and C respectively that link a repeating unit to another repeating unit of the PHU polymer. In various embodiments of the crosslinked PHU polymer, there is another crosslink comprising two diene-dienophile adducts at B and D respectively that link the repeating unit to another repeating unit of the PHU polymer. In various embodiments, there are two crosslinks linking a repeating unit of the PHU polymer to another repeating unit of the PHU polymer. In such embodiments, a first repeating unit of the PHU polymer is crosslinked with a second repeating unit of the PHU polymer at sites A and C, as well as at sites B and D.

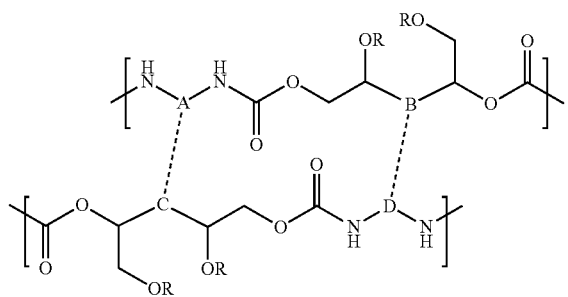

Scheme 1. Structure of a polyhydroxyurethane (PHU) polymer being crosslinked at sites A, B, C and D, wherein R is independently a H or a functional group which may be selected from but not limited to alkyl, sulfate, sulfonate, phosphate, carboxylate, sulfobetaine, phosphobetaine, cinnamate, fatty acid, aminoacid, lactic acid/polylactic acid, caprolactone/polycaprolactone, polysiloxane and the like and combinations thereof.

In various embodiments, only sites A and C are each a diene-dienophile adduct. In various embodiments, there is one crosslink linking a repeating unit of the PHU polymer to another repeating unit of the PHU polymer. In such embodiments, a first repeating unit of the PHU polymer is crosslinked with a second repeating unit of the PHU polymer at sites A and C.

In various embodiments, only sites B and D are each a diene-dienophile adduct. In various embodiments, there is one crosslink linking a repeating unit of the PHU polymer to another repeating unit of the PHU polymer. In such embodiments, a first repeating unit of the PHU polymer is crosslinked with a second repeating unit of the PHU polymer at sites B and D.

Although not shown in Scheme 1, in various embodiments, a first repeating unit of the PHU polymer may be linked to a second repeating unit of the PHU polymer with a crosslink comprising two diene-dienophile adducts at A and D respectively and a first repeating unit of the PHU polymer may be linked to a second repeating unit of the PHU polymer with a crosslink comprising two diene-dienophile adducts at B and C respectively.

Although there are only two crosslinks or four Diels-Alder adducts illustrated in Scheme 1, as will be appreciated, numerous sites (comprising a diene moiety) along the polymer chain may be crosslinked in a similar manner.

In various embodiments, the method of crosslinking a PHU polymer forms a crosslinked polymer having an extensive crosslinked network structure.

In various embodiments, a Diels-Alder adduct comprises a furan-maleimide adduct. In one embodiment, at least a part of the Diels-Alder adduct comprises a structure of that resembles the following structure (1):

Structure (I)

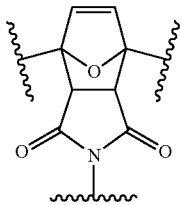

In various embodiments, the diene-dienophile adduct comprises a ring structure formed from a Diels-Alder reaction between the diene moiety and the dienophile moiety. In one embodiment, the ring structure is a substituted cyclohexene.

In various embodiments, any suitable diene moiety that effectively reacts with a dienophile in a Diels-Alder reaction to form Diels-Alder adducts may be used in embodiments of the method disclosed herein. In various embodiments, the diene moiety is selected from the group consisting of furan, thiophene, pyrrole, cyclopentadiene, thiophenoxide for e.g. thiophen-1-oxide, thiophene dioxide for e.g. thiophene-1,1-dioxide, cyclopentadienone for e.g. cyclopenta-2,4-dienone, pyran for e.g. 2H-pyran, cyclohexadiene for e.g. cyclohexa-1,3-diene, pyranoxide ring for e.g. 2H-pyran-1-oxide ring, dihydropyridine for e.g. 1,2-dihydropyridine, thiopyrandioxide for e.g. 2H-thiopyran-1,1-dioxide, cyclohexadienone for e.g. cyclohexa-2,4-dienone, muconic acid and pyranone such as pyran-2-one.

In various embodiments, the diene moiety comprises a furan moiety. In one embodiment, the diene moiety is disubstituted 2,5-furan.

In various embodiments, any suitable dienophile moiety that effectively reacts with a diene in a Diels-Alder reaction to form Diels-Alder adducts may be used in embodiments of the method disclosed herein. In various embodiments, the dienophile moiety is selected from the group consisting of cyclopentadiene, maleimide, isomaleimide, citraconimide, itaconimide and maleate.

In various embodiments, the dienophile moiety comprises a maleimide moiety.

In various embodiments, the crosslinking agent having two or more dienophile moieties comprises at least two, at least three, at least four, at least five, at least six, at least seven, at least eight, at least nine or at least ten maleimide moieties in said crosslinking agent. In various embodiments, the crosslinking agent may be a bismaleimide, trismaleimide, tetramaleimide or a polymaleimide.

In various embodiments, the crosslinking agent is a bismaleimide. The crosslinking agent may be a bismaleimide represented by general formula (I):

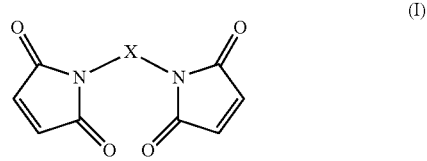

wherein X is a single bond or $C_1$-$C_{14}$ alkylene (i.e. —$(CH_2)_y$— where y is 1 to 14), polyethyleneglycol (PEG) or segments thereof, polypropylene glycol (PPG) or segments thereof, phenylene, methylenebis(phenylene) for e.g. (methylenedi-4,1-phenylene),

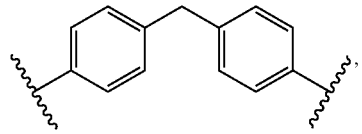 [SMILES: *c1ccc(Cc2ccc(*)cc2)cc1]

sulfonylbis(phenylene) for e.g. (sulfonyl-3,1-phenylene),

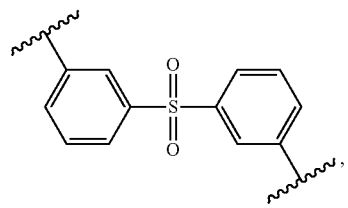 [SMILES: *c1cccc(S(=O)(=O)c2cccc(*)c2)c1]

oxybis(phenylene), for e.g. (oxydi-4,1-phenylene)

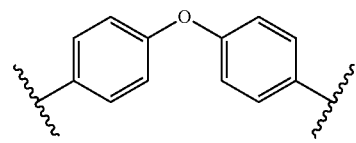 [SMILES: *c1ccc(Oc2ccc(*)cc2)cc1]

and combinations thereof. In various embodiments, the bismaleimide is selected from the group consisting of 1,1'-(Methylenedi-4,1-phenylene)bismaleimide, also known as 1,1'-(methylenebis(4,1-phenylene))bis(1H-pyrrole-2,5-dione) (BM1), N,N'-hexamethylenebismaleimide, also known as 1,1'-(hexane-1,6-diyl)bis(1H-pyrrole-2,5-dione) (BM2), N,N'-(1,4-Phenylene) dimaleimide, also known as 1,1'-(1,4-phenylene)bis(1H-pyrrole-2,5-dione) (BM3) and N,N'-pentamethylenebismaleimide, also known as 1,1'-(pentane-1,5-diyl)bis(1H-pyrrole-2,5-dione) (BM4).

In various embodiments, the step of reacting the crosslinking agent with the PHU polymer comprises mixing the PHU polymer and the crosslinking agent in an amount such that the molar ratio of the PHU polymer and the crosslinking agent is from about 1:0.05 to about 1:1. In various embodiments, the PHU polymer and the crosslinking agent are mixed/reacted in a molar ratio of about 1:0.05, molar ratio of about 1:0.075, molar ratio of about 1:0.10, molar ratio of about 1:0.125, molar ratio of about 1:0.15, molar ratio of about 1:0.175, molar ratio of about 1:0.20, molar ratio of about 1:0.225, molar ratio of about 1:0.25, molar ratio of about 1:0.275, molar ratio of about 1:0.30, molar ratio of about 1:0.325, molar ratio of about 1:0.350, molar ratio of about 1:0.375, molar ratio of about 1:0.40, molar ratio of about 1:0.425, molar ratio of about 1:0.45, molar ratio of about 1:0.475, molar ratio of about 1:0.50, molar ratio of about 1:0.525, molar ratio of about 1:0.550, molar ratio of about 1:0.575, molar ratio of about 1:0.60, molar ratio of about 1:0.625, molar ratio of about 1:0.65, molar ratio of about 1:0.675, molar ratio of about 1:0.70, molar ratio of about 1:0.725, molar ratio of about 1:0.75, molar ratio of about 1:0.775, molar ratio of about 1:0.80, molar ratio of about 1:0.825, molar ratio of about 1:0.85, molar ratio of about 1:0.875, molar ratio of about 1:0.90, molar ratio of about 1:0.925, molar ratio of about 1:0.95, molar ratio of about 1:0.975, or a molar ratio of about 1:1. In some embodiments, the PHU polymer and the crosslinking agent are reacted in a molar ratio of about 1:0.05, about 1:0.1, about 1:0.125, about 1:0.25, about 1:0.5 or about 1:1. In some embodiments, the PHU polymer and the crosslinking agent are reacted in a molar ratio of about 20:1, about 10:1, about 8:1, about 4:1 or about 2:1.

In various embodiments, the PHU polymer has a number average molecular weight in the range of from about 2,000 g/mol to about 50,000 g/mol, from about 2,500 g/mol to about 45,000 g/mol, from about 3,000 g/mol to about 40,000 g/mol, from about 3,500 g/mol to about 35,000 g/mol, from about 4,000 g/mol to about 30,000 g/mol, from about 4,500 g/mol to about 25,000 g/mol, from about 5,000 g/mol to about 20,000 g/mol, from about 5,500 g/mol to about 15,000 g/mol, from about 6,000 g/mol to about 10,000 g/mol, from about 6,500 g/mol to about 9,500 g/mol, from about 7,000 g/mol to about 9,000 g/mol, from about 7,500 g/mol to about 8,500 g/mol or about 8,000 g/mol. In some embodiments, the PHU polymer has a number average molecular weight of about 2,540 g/mol, about 2,670 g/mol, about 2,690 g/mol, about 3,020 g/mol, about 3,200 g/mol, about 3,410 g/mol, about 3,920 g/mol, about 4,350 g/mol, about 4,890 g/mol, about 5,040 g/mol, about 5,220 g/mol or about 12,731 g/mol. In other embodiments, the PHU polymer has a number average molecular weight of about 2,500 g/mol, about 2,620 g/mol, about 2,700 g/mol, about 3,100 g/mol, about 3,440 g/mol, about 3,630 g/mol, about 3,750 g/mol, about 4,320 g/mol, about 4,560 g/mol, about 4,680 g/mol, about 4,760 g/mol, about 6,190 g/mol or about 6,980 g/mol.

In various embodiments, the PHU polymer has a polydispersity index (PDI) in the range of from about 1.0 to about 5.0, from about 1.1 to about 4.9, from about 1.2 to about 4.8, from about 1.3 to about 4.7, from about 1.4 to about 4.6, from about 1.5 to about 4.5, from about 1.6 to about 4.4, from about 1.7 to about 4.3, from about 1.8 to about 4.2, from about 1.9 to about 4.1, from about 2.0 to about 4.0, from about 2.1 to about 3.9, from about 2.2 to about 3.8, from about 2.3 to about 3.7, from about 2.4 to about 3.6, from about 2.5 to about 3.5, from about 2.6 to about 3.4, from about 2.7 to about 3.3, from about 2.8 to about 3.2, from about 2.9 to about 3.1 or about 3.0. In some embodiments, the PHU polymer has a PDI of about 1.31, about 1.32, about 1.35, about 1.37, about 1.49, about 1.56, about 1.64, about 1.74, about 1.85 or about 2.21. In other embodiments, the PHU polymer has a PDI of about 1.41, about 1.45, about 1.50, about 1.51, about 1.55, about 1.60, about 1.67, about 1.68, about 1.70, about 1.75, about 1.80, about 1.99, about 2.01 or about 2.04.

In various embodiments, the PHU polymer has a glass transition temperature (Tg) in the range of from about −30° C. to about 80° C., from about −25° C. to about 75° C., from about −20° C. to about 70° C., from about −15° C. to about 65° C., from about −10° C. to about 60° C., from about −5° C. to about 55° C., from about 0° C. to about 50° C., from about 5° C. to about 45° C., from about 10° C. to about 40° C., from about 15° C. to about 35° C., from about 20° C. to about 30° C., or about 25° C. In some embodiments, the PHU polymer has a glass transition temperature (Tg) of about −7° C., about −3° C., about −1° C., about 5° C., about 10° C., about 14° C., about 19° C., about 22° C., about 24.5° C., about 42° C. or about 51° C.

In various embodiments, the method of crosslinking a PHU polymer disclosed herein is a post-polymerisation crosslinking method.

In various embodiments, the method further comprises reacting a biscarbonate with an amine containing compound to form the PHU polymer, prior to reacting the PHU polymer with the crosslinking agent, wherein at least one of the biscarbonate or amine containing compound comprises a diene moiety.

In various embodiments, the step of reacting a biscarbonate with an amine containing compound to form the PHU polymer comprises reacting at least one biscarbonate, at least two biscarbonate, at least three biscarbonate or at least four biscarbonate with at least one amine containing compound, at least two amine containing compounds, at least three amine containing compounds or at least four amine containing compounds. In various embodiments, a biscarbonate is reacted with two amine containing compounds to form the PHU polymer. As may be appreciated, the two amine containing compounds may be added in a variety of different ratios, depending on the desired functionality to be achieved. The two amine containing compounds may be added in a molar ratio of from about 1:1 to about 4:1. The two amine containing compounds may be added in a molar ratio of about 1:1, about 1:2, about 1:3, about 1:4, about 2:1, about 2:3, about 3:1, about 3:2, about 3:4, about 4:1 or about 4:3. In some embodiments, the two amine containing compounds are added in a molar ratio of about 1:3 or about 3:1.

In various embodiments, the biscarbonate comprises at least one, at least two, at least three, at least four, at least five, at least six, at least seven, at least eight, at least nine or at least ten diene moieties. In various embodiments, the amine containing compound comprises at least one, at least two, at least three, at least four, at least five, at least six, at least seven, at least eight, at least nine or at least ten diene moieties. In some embodiments, the biscarbonate comprises one or more diene moieties and the amine containing compound does not comprise diene moiety. In some embodiments, the biscarbonate does not comprise diene moiety and the amine containing compound comprises one or more diene moieties. In some embodiments, both the biscarbonate and amine containing compound each comprises one or more diene moieties.

In various embodiments, the diene moiety comprises a furan moiety.

In some embodiments, the biscarbonate comprises one or more furan moieties and the amine containing compound does not comprise furan moiety. In such embodiments, the biscarbonate is a furan-based cyclic biscarbonate selected from the group consisting of bis((2-oxo-1,3-dioxolan-4-yl)methyl)furan-2,5-dicarboxylate (FBC1) and 4,4'-(((furan-2,5-diylbis(methylene))bis(oxy))bis-(methylene))bis(1,3-dioxolan-2-one) (FBC2), and the amine containing compound is selected from the group consisting of xylene diamine (XDA), diaminopentane (DAP) and hexamethylenediamine (HDA). In some embodiments, the biscarbonate compound does not comprise furan moiety and the amine containing compound comprises one or more furan moieties. In such embodiments, the biscarbonate is selected from the group consisting of sebacate bis-carbonate (SBC), terephthalic bis-carbonate (TBC), benzene bis-carbonate (BBC), methyl bis-carbonate (MBC), succinic bis-carbonate (SuBC), bis((2-oxo-1,3-dioxolan-4-yl)methyl)pyridine-2,5-dicarboxylate (PBC), bis((2-oxo-1,3-dioxolan-4-yl)methyl)pyridine-2,6-dicarboxylate (PBC2) and 4,4'-(((tetrahydrofuran-3,4-diyl)bis(oxy))bis-(methylene))bis(1,3-dioxolan-2-one) (HFBC), and the amine containing compound is a furan bisamine (FBA). In other embodiments, both the biscarbonate and the amine containing compound each comprises one or more diene moieties. In such embodiments, the biscarbonate is a furan-based cyclic biscarbonate selected from the group consisting of bis((2-oxo-1,3-dioxolan-4-yl)methyl)furan-2,5-dicarboxylate (FBC1) and 4,4'-(((furan-2,5-diylbis(methylene))bis(oxy))bis-(methylene))bis(1,3-dioxolan-2-one) (FBC2), and the amine containing compound is a furan bisamine (FBA).

In various embodiments, the biscarbonate compound is selected from the following:

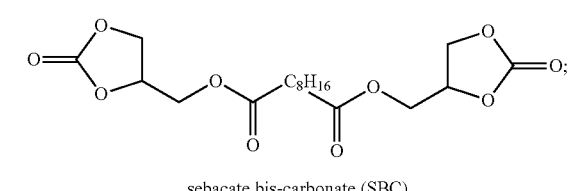

sebacate bis-carbonate (SBC)

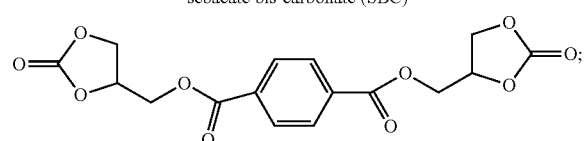

terephthalic bis-carbonate (TBC)

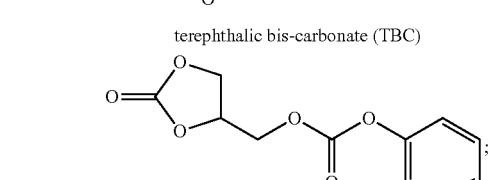

benzene bis-carbonate (BBC)

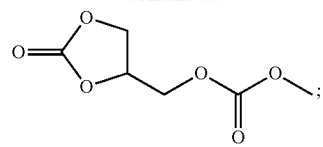

methyl bis-carbonate (MBC)

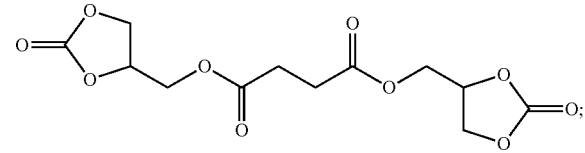

succinic bis-carbonate (SuBC)

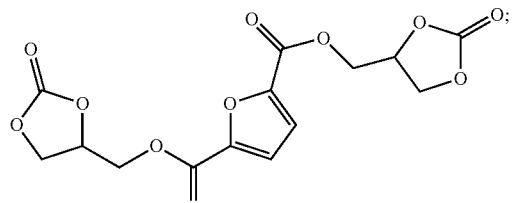

bis((2-oxo-1,3-dioxolan-4-yl)methyl)furan-2,5-dicarboxylate (FBC1)

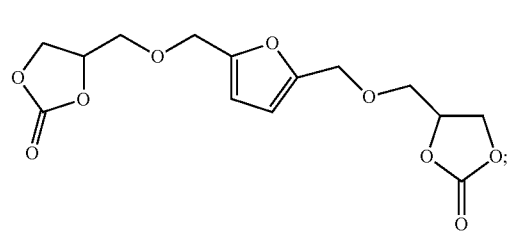

4,4'-(((furan-2,5-diylbis(methylene))bis(oxy))bis(methylene))bis(1,3-dioxolan-2-one) (FBC2)

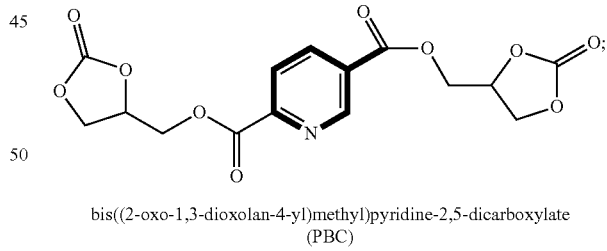

bis((2-oxo-1,3-dioxolan-4-yl)methyl)pyridine-2,5-dicarboxylate (PBC)

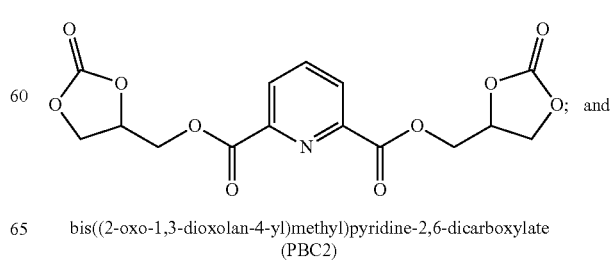

bis((2-oxo-1,3-dioxolan-4-yl)methyl)pyridine-2,6-dicarboxylate (PBC2)

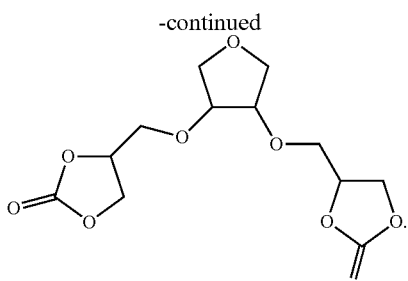

4,4'-(((tetrahydrofuran-3,4-diyl)bis(oxy))bis(methylene))bis(1,3-dioxolan-2-one) (HFBC)

In various embodiments, the amine containing compound comprises at least two amine functional groups. The amine containing compound may be an aliphatic diamine/bis-amine or an aromatic diamine/bis-amine.

In various embodiments, the amine containing compound is a diamine/bis-amine selected from the group consisting of furan bis-amine (FBA), xylene diamine (XDA), diaminopentane (DAP) and hexamethylenediamine (HDA).

In various embodiments, the biscarbonate is selected from the group consisting of sebacate bis-carbonate (SBC), terephthalic bis-carbonate (TBC), benzene bis-carbonate (BBC), methyl bis-carbonate (MBC), succinic bis-carbonate (SuBC), bis((2-oxo-1,3-dioxolan-4-yl)methyl)furan-2,5-dicarboxylate (FBC1), 4,4'-(((furan-2,5-diylbis(methylene))bis(oxy))bis(methylene))bis(1,3-dioxolan-2-one) (FBC2), bis((2-oxo-1,3-dioxolan-4-yl)methyl)pyridine-2,5-dicarboxylate (PBC), bis((2-oxo-1,3-dioxolan-4-yl)methyl)pyridine-2,6-dicarboxylate (PBC2), 4,4'-(((tetrahydrofuran-3,4-diyl)bis(oxy))bis(methylene))bis(1,3-dioxolan-2-one) (HFBC), and the amine containing compound is selected from the group consisting of furan bis-amine (FBA), xylene diamine (XDA), diaminopentane (DAP) and hexamethylenediamine (HDA).

In various embodiments, the PHU polymer is a functionalized PHU polymer. The PHU polymer obtained from reacting a biscarbonate with an amine containing compound may be functionalized with one or more substituents selected from alkyl, sulfate, sulfonate, phosphate, carboxylate, sulfobetaine, phosphobetaine, cinnamate, fatty acid, aminoacid, lactic acid/polylactic acid, caprolactone/polycaprolactone, polysiloxane and the like and combinations thereof.

In various embodiments, the biscarbonate is prepared from a bio-based source/bio-originated source. In various embodiments, a precursor compound is first derived from a bio-based source before converting the precursor compound into biscarbonate for use in polymerisation of the PHU polymer. In various embodiments, the step of deriving a precursor compound from a bio-based source comprises subjecting the bio-based source to a variety of chemical, physical and/or biological steps/reactions/processes. In various embodiments, the chemical and/or biological reactions comprise biocatalysis, fermentation and dehydration, optionally catalysed with an acid or a base. Physical steps or processes may include milling, grinding, crushing, pulverizing or the like. In various embodiments, the step of deriving the precursor compound comprises deriving the precursor compound from a bio-based source selected from lignin, hexose, glucose and erythritol.

In various embodiments, the precursor compound is an emerging renewable chemical derived from bio-based source. In various embodiments, the precursor compound is selected from the group consisting of 5-hydroxymethylfurfural (HMF), furan-2,5-diyldimethanol (FDME), furan-2,5-dicarboxylic acid (FDCA), furan-2,5-diyldimethanamine (FDMA), pyridine-2,5-dicarboxylic acid, pyridine-2,6-dicarboxylic acid, 1,4-anhydroerythritol and terephthalic acid (TPA). In various embodiments, FDME, FDCA and FDMA are derivatives of HMF.

In various embodiments, the amine containing compound is prepared from a bio-based source.

In various embodiments, the bio-based source comprises biomass selected from plant-based polymers, amino acids and sugar molecules. In some embodiments, the plant-based polymer comprises phenolic groups. In one embodiment, the plant-based polymer is lignin. In some embodiments, the sugar molecules are selected from the group consisting of hexose, glucose, fructose, and erythritol.

In various embodiments, the bio-based source is biomass feedstock.

In various embodiments, the bio-based source may also be selected from plant oils (triglycerides of oleic, linoleic and linolenic acids), terpenes, glycerol or other —OH derivatives, di-carboxylic acids like sebacic acid and adipic acid etc.

In various embodiments, the bis-carbonate and/or bis-amine and/or PHU polymer and/or crosslinked PHU polymer disclosed herein are not derived from petroleum-based source. In various embodiments, at least one of the bis-carbonate or bis-amine disclosed herein is not derived from petroleum-based source. Accordingly, in various embodiments, the PHU polymer and/or crosslinked PHU polymer disclosed herein may be partially bio-based/bio-derived or fully bio-based/bio-derived.

In various embodiments, the method is substantially devoid of a step containing the use of macromonomers and/or oligomers and/or multi functional macromonomers as starting materials for polymerisation. In various embodiments, the method is substantially devoid of a step containing post-functionalization of a polymer and/or light and/or high temperatures (for e.g. above about 150° C.) for curing a polymer. Advantageously, embodiments of the method disclosed herein provides an easy and straightforward way of crosslinking a polyhydroxyurethane (PHU) polymer, thereby making the crosslinking process cost-effective and economical on a large scale.

In various embodiments, the method involves the use of partially bio-based components and/or some but not all bio-based monomers. In other embodiments, the method is substantially devoid of a step containing the use of partially bio-based components and/or bio-based small molecular monomers such as fatty acid based cyclic carbonate monomers.

In various embodiments, the components used in the method disclosed herein are completely bio-based. In various embodiments therefore, due to the very high bio-content as compared to conventional polymers, the crosslinked polymers disclosed herein are innocuous biocompatible polymers, making them attractive as alternative sustainable materials for future applications such as in coatings, foams and as adhesives. Therefore in embodiments of the method disclosed herein where at least the biscarbonate, amine containing monomers, polyhydroxyurethanes and cross-linked polyhydroxyurethanes are completely bio-based/bio-derived/bio-originated, these embodiments are advantageous over existing technologies in that they are environmentally more friendly.

In various embodiments, the method disclosed herein is non-toxic and isocyanate-free. In various embodiments therefore, the method disclosed herein is less toxic, relatively safer and more environmentally friendly than conventional methods.

In various embodiments, there is provided a crosslinked polyhydroxyurethane (PHU) polymer obtained from the method disclosed herein, the crosslinked polymer comprising a plurality of diene-dienophile adducts.

In various embodiments, the crosslinked PHU polymer has a degree of crosslinking in the range of from about 1% to about 80%, from about 5% to about 75%, from about 10% to about 70%, from about 15% to about 65%, from about 20% to about 60%, from about 25% to about 55%, from about 30% to about 50%, from about 35% to about 45% or about 40%. In some embodiments, the degree of crosslinking is about 5%, about 15%, about 25%, about 29%, about 35%, about 50% or about 53%.

In various embodiments, the crosslinked PHU polymer has a crosslinking density in the range of from about 0.05 $mmol/cm^3$ to about 10.0 $mmol/cm^3$, from about 0.1 $mmol/cm^3$ to about 9.5 $mmol/cm^3$, from about 0.2 $mmol/cm^3$ to about 9.0 $mmol/cm^3$, from about 0.3 $mmol/cm^3$ to about 8.5 $mmol/cm^3$, from about 0.4 $mmol/cm^3$ to about 8.0 $mmol/cm^3$, from about 0.5 $mmol/cm^3$ to about 7.5 $mmol/cm^3$, from about 1.0 $mmol/cm^3$ to about 7.0 $mmol/cm^3$, from about 1.5 $mmol/cm^3$ to about 6.5 $mmol/cm^3$, from about 2.0 $mmol/cm^3$ to about 6.0 $mmol/cm^3$, from about 2.5 $mmol/cm^3$ to about 5.5 $mmol/cm^3$, from about 3.0 $mmol/cm^3$ to about 5.0 $mmol/cm^3$, from about 3.5 $mmol/cm^3$ to about 4.5 $mmol/cm^3$ or about 4.0 $mmol/cm^3$. In some embodiments, the crosslinking density is about 0.2 $mmol/cm^3$, about 0.6 $mmol/cm^3$, about 1.0 $mmol/cm^3$, about 1.4 $mmol/cm^3$ or about 2.0 $mmol/cm^3$.

In various embodiments, the crosslinked PHU polymer may be one that is obtained by the method described above. Accordingly, in various embodiments, the crosslinked PHU polymer and the diene-dienophile adducts contain one or more features or share one or more properties that are similar to those described above. The diene and dienophile moieties may also contain one or more features or share one or more properties that are similar to those described above.

In various embodiments, the crosslinked PHU polymer contains crosslinks at various sites similar to that described in Scheme 1 above. As may be appreciated, there may be one crosslink, two crosslinks or more than two crosslinks linking a repeating unit of the PHU polymer to another repeating unit of the PHU polymer, depending on the number of diene moiety (such as furan) present in the PHU polymer.

Embodiments of the crosslinked PHU polymer disclosed herein are structurally different from traditional polyurethanes at least in that embodiments of the crosslinked PHU polymer contain hydroxyl groups. In various embodiments, the crosslinked PHU polymers disclosed herein are non-isocyanate polyhydroxyl-urethanes (NIPUs/PHUs) comprising free secondary or primary hydroxyl functional groups in their structure in addition to the carbamate linkages. In various embodiments, the crosslinked PHU polymers are hydrophilic. Without being bound by theory, it is believed that the hydroxyl groups present within the reaction product increase the adhesion properties and can be further functionalized or cross-linked. Without being bound by theory, it is also believed that the presence of hydrogen bonds will increase the thermal and hydrolytic stability as well as chemical resistance to solvents. As compared to conventional PU polymers, or particularly PHU polymers, embodiments of the crosslinked PHU polymers have higher degradation temperature and higher chemical stability to hydrolysis.

Advantageously, as compared to conventional PU polymers, or particularly PHU polymers, embodiments of the crosslinked PHU polymers have higher molecular weight. As compared to conventional PU polymers, or particularly PHU polymers, embodiments of the crosslinked PHU polymers display better and improved resistance to water and organic solvents.

In various embodiments, the crosslinked polymer is devoid of an isocyanate group, thereby making the production process friendly to the environment.

In various embodiments, the crosslinked PHU polymers disclosed herein are thermosetting polymers, making them attractive for use as resins for solvent-borne coatings on a wide range of substrate surfaces.

In various embodiments, the Diels-Alder reaction is reversible upon exposure to a stimulus such as heat. In various embodiments, the diene-dienophile adducts can be reversibly thermally cleaved to regenerate the starting materials (i.e., diene and dienophile). In such embodiments, the reverse Diels-Alder reaction is a retro Diels-Alder reaction.

In various embodiments, the crosslinks are capable of being removed at a temperature that is more than about 50° C., more than about 60° C., more than about 70° C., more than about 80° C., more than about 90° C., more than about 100° C., more than about 110° C. or more than about 120° C. In various embodiments, the crosslinks are removable at a temperature that is more than about 50° C., more than about 55° C., more than about 60° C., more than about 65° C., more than about 70° C., more than about 75° C., more than about 80° C., more than about 85° C., more than about 90° C., more than about 91° C., more than about 92° C., more than about 93° C., more than about 94° C., more than about 95° C., more than about 96° C., more than about 97° C., more than about 98° C., more than about 99° C., more than about 100° C., more than about 101° C., more than about 102° C., more than 103° C., more than about 104° C., more than about 105° C., more than about 106° C., more than about 107° C., more than about 108° C., more than about 109° C., more than about 110° C., more than about 111° C., more than about 112° C., more than 113° C., more than about 114° C., more than about 115° C., more than about 116° C., more than about 117° C., more than about 118° C., more than about 119° C., more than about 120° C., more than about 130° C., more than about 140° C., more than about 150° C., more than about 160° C., more than about 170° C., more than about 180° C., more than about 190° C. or more than about 200° C. In various embodiments, the crosslinks are removable at a temperature of from more than about 90° C. to about 200° C., from about 95° C. to about 195° C., from about 100° C. to about 190° C., from about 105° C. to about 185° C., from about 110° C. to about 180° C., from about 115° C. to about 175° C., from about 120° C. to about 170° C., from about 125° C. to about 165° C., from about 130° C. to about 160° C., from about 135° C. to about 155° C., from about 140° C. to about 150° C., or about 145° C. In some embodiments, the crosslinks are removed from the PHU polymer at a temperature of about 110° C. or about 120° C. It will be appreciated that the temperature at which the crosslinks are removed from the PHU polymer may be lowered by tuning the diene-dienophile structure/adduct.

In various embodiments, when the crosslinked PHU polymer is heated at a temperature that is more than about 50° C., more than about 60° C., more than about 70° C., more than about 80° C., more than about 90° C., more than about 100° C., more than about 110° C. or more than about 120° C., a retro Diels-Alder reaction takes place and the weak crosslinks between the repeating units of the crosslinked PHU polymer break apart/dissociate to yield a PHU polymer and a crosslinking agent. In various embodiments therefore, the crosslinked PHU polymers are capable of reverting to their thermoplastic precursors by heating. Advantageously, embodiments of the crosslinked PHU polymer allow for the reversible conversion from a thermosetting polymer to thermoplastic.

In various embodiments, the crosslinked PHU polymer comprises thermo-reversible or thermally reversible cross-link networks.

In various embodiments therefore, the crosslinked polymer disclosed herein is a recyclable polymer. In various embodiments, the crosslinked polymer disclosed herein is capable of being applied or deposited as a layer of coating that is recyclable. Advantageously, in various embodiments, recycling of a crosslinked PHU polymer film can be performed via retro Diels-Alder reaction by simply heating the films at an elevated temperature.

In various embodiments, the crosslinked polymer is capable of being applied or deposited as a layer of coating that is healable, for e.g. it can be restored to its previous condition even after being subjected to abrasion such as a scratch, cut or tear. In various embodiments, the crosslinked polymer disclosed herein has self healing properties. Advantageously, in various embodiments, a scratched crosslinked polymer coating is capable of healing on its own without the requirement of any external heat source or addition of any external chemical reagents. In various embodiments, the crosslinked polymer disclosed herein has thermo healing properties. A scratched crosslinked polymer coating may heal faster with the application of heat.

In various embodiments, the crosslinked polymer is a shape memory polymer. Advantageously, in various embodiments, the crosslinked polymer is capable of returning from a deformed/distorted state to its original shape without the requirement of any stimulus such as temperature change etc. For example, a crosslinked product that has been folded/twisted/rolled can convert easily into its original flat shape. The time taken for the conversion may be sped up by the application of heat.

In various embodiments, the crosslinked polymer is a shape memory polymer that has the capability of being programmed to store the memory of a shape that is different from its original shape. Advantageously, in various embodiments, the crosslinked polymer is capable of returning from a deformed/distorted state to its stored/fixed/set shape. In various embodiments, there is provided a method of setting the shape of a PHU polymer, the method comprising moulding the polymer to a desired shape at a temperature of more than about 50° C. or more than about 90° C.; and lowering the temperature to no more than about 90° C. or no more than about 50° C. to set the shape of the polymer.

In various embodiments, the crosslinked polymer disclosed herein is advantageous over known vinyl functional PHUs/NIPUs at least in that the cross-linked polyhydroxyurethanes prepared according to the method disclosed herein are room temperature curing.

Advantageously, in various embodiments of the method disclosed herein, the structure and composition of the PHU polymer, and the amount of the crosslinker agent may be carefully tuned to produce a crosslinked PHU polymer that have self-healing characteristics (at room temperature or elevated temperature) and shape memory properties.

In various embodiments, the crosslinked polymer is light brown in color. Advantageously, the coloration may be reduced by precise selection of the combination of the monomers (i.e. biscarbonate and amine containing compound) used during polymerisation.

In various embodiments, there is provided a method of undoing, reversing or removing the crosslinks of a crosslinked polyhydroxyurethane (PHU) polymer comprising a plurality of diene-dienophile adducts, the method comprising: heating the crosslinked PHU polymer at a temperature of more than about 50° C. to undo, reverse or remove the crosslinks.

In various embodiments, the step of heating the crosslinked PHU polymer is performed at a temperature that is more than about 50° C., more than about 60° C., more than about 70° C., more than about 80° C., more than about 90° C., more than about 100° C., more than about 110° C. or more than about 120° C. In various embodiments, the step of heating the crosslinked PHU polymer is performed at a temperature that is more than about 50° C., more than about 55° C., more than about 60° C., more than about 65° C., more than about 70° C., more than about 75° C. more than about 80° C., more than about 85° C., more than about 90° C., more than about 91° C., more than about 92° C., more than about 93° C., more than about 94° C., more than about 95° C., more than about 96° C., more than about 97° C., more than about 98° C., more than about 99° C., more than about 100° C., more than about 101° C., more than about 102° C., more than 103° C., more than about 104° C., more than about 105° C., more than about 106° C., more than about 107° C., more than about 108° C., more than about 109° C., more than about 110° C., more than about 111° C., more than about 112° C., more than 113° C., more than about 114° C., more than about 115° C., more than about 116° C., more than about 117° C., more than about 118° C., more than about 119° C., more than about 120° C., more than about 130° C., more than about 140° C., more than about 150° C., more than about 160° C., more than about 170° C., more than about 180° C., more than about 190° C. or more than about 200° C. In various embodiments, the heating step is performed at a temperature of from more than about 90° C. to about 200° C., from about 95° C. to about 195° C., from about 100° C. to about 190° C., from about 105° C. to about 185° C., from about 110° C. to about 180° C., from about 115° C. to about 175° C., from about 120° C. to about 170° C., from about 125° C. to about 165° C., from about 130° C. to about 160° C., from about 135° C. to about 155° C., from about 140° C. to about 150° C., or about 145° C. In some embodiments, the heating step is carried out at a temperature of about 110° C. or about 120° C. It will be appreciated that the heating step may be carried out at a lower temperature by tuning the diene-dienophile structure(s)/adduct(s).

In various embodiments, the step of heating the crosslinked PHU polymer is performed for a time period of at least about 5 mins, at least about 10 mins, at least about 15 mins, at least about 20 mins, at least about 25 mins, at least about 30 mins, at least about 35 mins, at least about 40 mins, at least about 45 mins, at least about 50 mins, at least about 55 mins, at least about 1 hour, at least about 2 hours, at least about 3 hours, at least about 4 hours, at least about 5 hours, at least about 6 hours, at least about 7 hours, at least about 8 hours, at least about 9 hours, at least about hours, at least about 11 hours, at least about 12 hours, at least about 13 hours, at least about 14 hours, at least about 15 hours, at least about 16 hours, at least about 17 hours, at least about 18 hours, at least about 19 hours, at least about 20 hours, at least about 21 hours, at least about 22 hours, at least about 23 hours, or at least about 24 hours. In some embodiments, the heating step is carried for a time period of about 1 hour, 2 hours or about 3 hours.

In various embodiments, there is provided a composition/mixture comprising a polyhydroxyurethane (PHU) polymer having a plurality of diene moieties, a crosslinking agent having two or more dienophile moieties and an organic solvent. In various embodiments, the PHU polymer, crosslinking agent and organic solvent are similar to those described above. Advantageously, the composition/mixture comprising said PHU polymer, crosslinking agent and organic solvent is capable of being applied or deposited as a layer of coating/film on a wide variety of substrate surfaces such that the substrate eventually comprises a crosslinked PHU coating/film thereon.

In various embodiments, there is provided an article comprising a substrate and a layer of crosslinked PHU coating/film on/over said substrate. The substrate may be selected from a range of materials such as wood, glass, metal, plastic and fabric or the like. In some embodiments, the metal comprises aluminium, steel and the like and combinations thereof.

In various embodiments, there is provided a kit comprising a polyhydroxyurethane (PHU) polymer having a plurality of diene moieties, a crosslinking agent having two or more dienophile moieties and a solvent.

In various embodiments, the components present in the kit are packed separately from each other. The kit may be present as a 2 pack system, the first pack comprising a PHU polymer in a solvent, for e.g. in an organic solvent and the second pack comprising a crosslinking agent.

In various embodiments, there is provided a method of mixing a PHU polymer having a plurality of diene moieties, a crosslinking agent having two or more dienophile moieties and an organic solvent in situ to form a composition/mixture before applying to a substrate surface. Accordingly, in various embodiments, there is also provided a preparation kit for preparing the crosslinked PHU polymer, the kit comprising the PHU polymer; the crosslinking agent; and the organic solvent.

In various embodiments, the components present in the kit are packed together. The kit may be present as a one pack system, the pack comprising a PHU polymer and a blocked crosslinking agent in a solvent, for e.g. in an organic solvent. The blocked crosslinking agent may be blocked bis-/tri- or multi-maleimide crosslinkers. As may be appreciated, application of heat may be required to release free crosslinking agent from its blocked form, i.e. in a deblocking process in order for the crosslinking agent to react with the PHU polymer. Therefore, in embodiments of the one pack system disclosed herein where blocked crosslinking agent is used, crosslinking occurs at a higher temperature (such as at a temperature above ambient room temperature or at a temperature of more than about 90° C.).

BRIEF DESCRIPTION OF FIGURES

FIG. 3A shows a self-standing (crosslinked) PHU film using polymer P16 and BM1 ([Furan]:[BM1]=1:0.25). FIG. 3B shows a PHU coated steel substrate produced via dip-coating using polymer P16 and BM1 ([Furan]:[BM1]=1:0.25).

EXAMPLES

Figure 1:
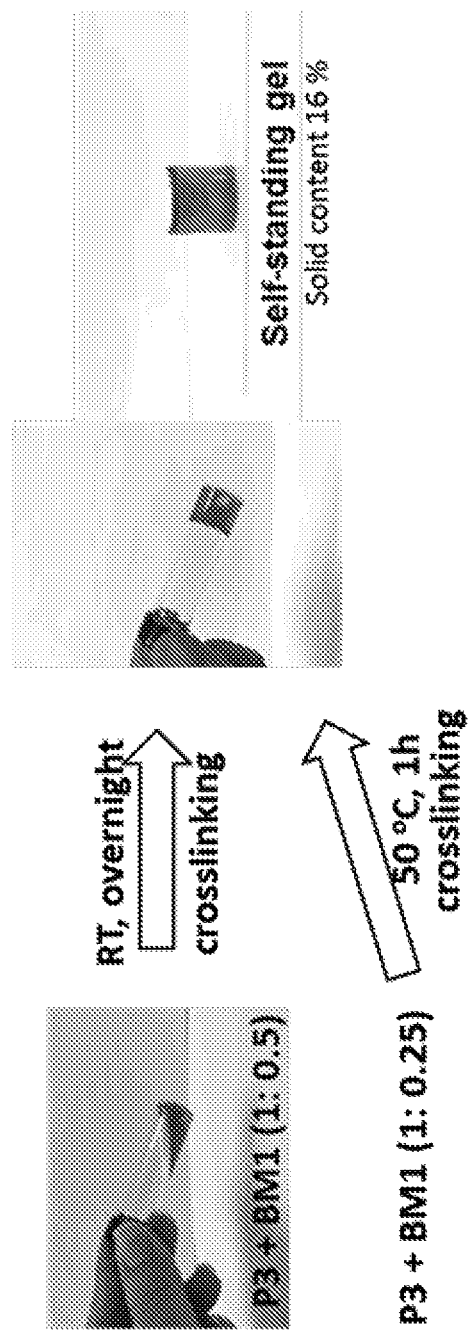
FIG. 1 shows images of crosslinked PHUs/NIPUs contained in a vial in accordance with various embodiments disclosed herein. As shown, P3 and BM1 were mixed (i) in a molar ratio of 1:0.5 at room temperature and allowed to crosslink overnight; and (ii) in a molar ratio of 1:0.25 at 50° C. for an hour to yield a self-standing gel with a solid content of 16%.

Example embodiments of the disclosure will be better understood and readily apparent to one of ordinary skill in the art from the following examples, tables and if applicable, in conjunction with the figures.

Polyhydroxyurethanes (PHUs) or non-isocyanate polyurethanes (NIPUs) are the emerging class of polymer synthesized via a non-toxic or non-isocyanate based synthetic routes by utilizing di/poly-cyclic carbonates and di/poly-amines. These PHUs or NIPUs are the potential alternatives to traditional PUs. These polymers are reported to have high degradation temperature, high chemical stability towards hydrolysis and charactestics solubility behaviour. The use of bio-based cyclic carbonates and amine monomers will make the resultant PHUs/NIPUs further greener, safer, bio-renewable and bio-compatible materials. However, a common limitation of these PHUs synthesized from bis-carbonate and bis-amine monomers is the low molecular weight nature, which renders these PHUs being applied for coating applications.

The inventors have found that one of the ways to overcome this issue is to adapt easy crosslinking strategies of PHUs via a post-polymerization crosslinking reaction.

Accordingly, the following examples describe a method of preparing a PHU polymer having a plurality of diene moieties from a bio-based source and a method of crosslinking a PHU polymer in an environmentally benign process in accordance with various embodiments of the present disclosure.

In the following examples, it is shown that PHUs/NIPUs based coatings can be formulated by post-polymerization crosslinking. Furan containing PHUs/NIPUs were synthesized and post-polymerization crosslinking of these PHUs/NIPUs was achieved by reacting with bis-maleimides under ambient conditions via Diels-Alder reaction in the absence of catalyst.

As will be shown in the following examples, embodiments of the presently disclosed method obtained crosslinked PHU polymers that are capable of addressing several problems of conventional methods used in the art. In the examples, the solutions of PHUs with bis-maleimides produced uniform film when applied over substrates such as glass, metal (Al/steel), plastic or wooden substrates. The crosslinked coating films disclosed herein have also shown to have improved water and solvent resistance properties as compared to their non-crosslinked counterparts. Most interestingly, it is shown that these crosslinked coating films can be recycled thermally via retro Diels-Alder reaction by simply heating the films at elevated temperature. Advantageously, the crosslinked PHU polymers have also shown to display self-healing characteristics and shape memory properties.

It should be appreciated that the examples provided below are meant to be merely illustrative and not in any way meant to be exhaustive or restrictive.

In the following examples, furan containing PHUs were synthesized and post-polymerization crosslinking of these PHUs were achieved by the reaction with bis-maleimide (via Diels-Alder reaction) under ambient conditions. Interestingly, these crosslinked coating films can be recycled thermally via retro Diels-Alder reaction by simply heating the films at elevated temperature. The synthesis procedures of the Examples generally follow and/or may be represented by one or more of the following schemes.

Figure 11:
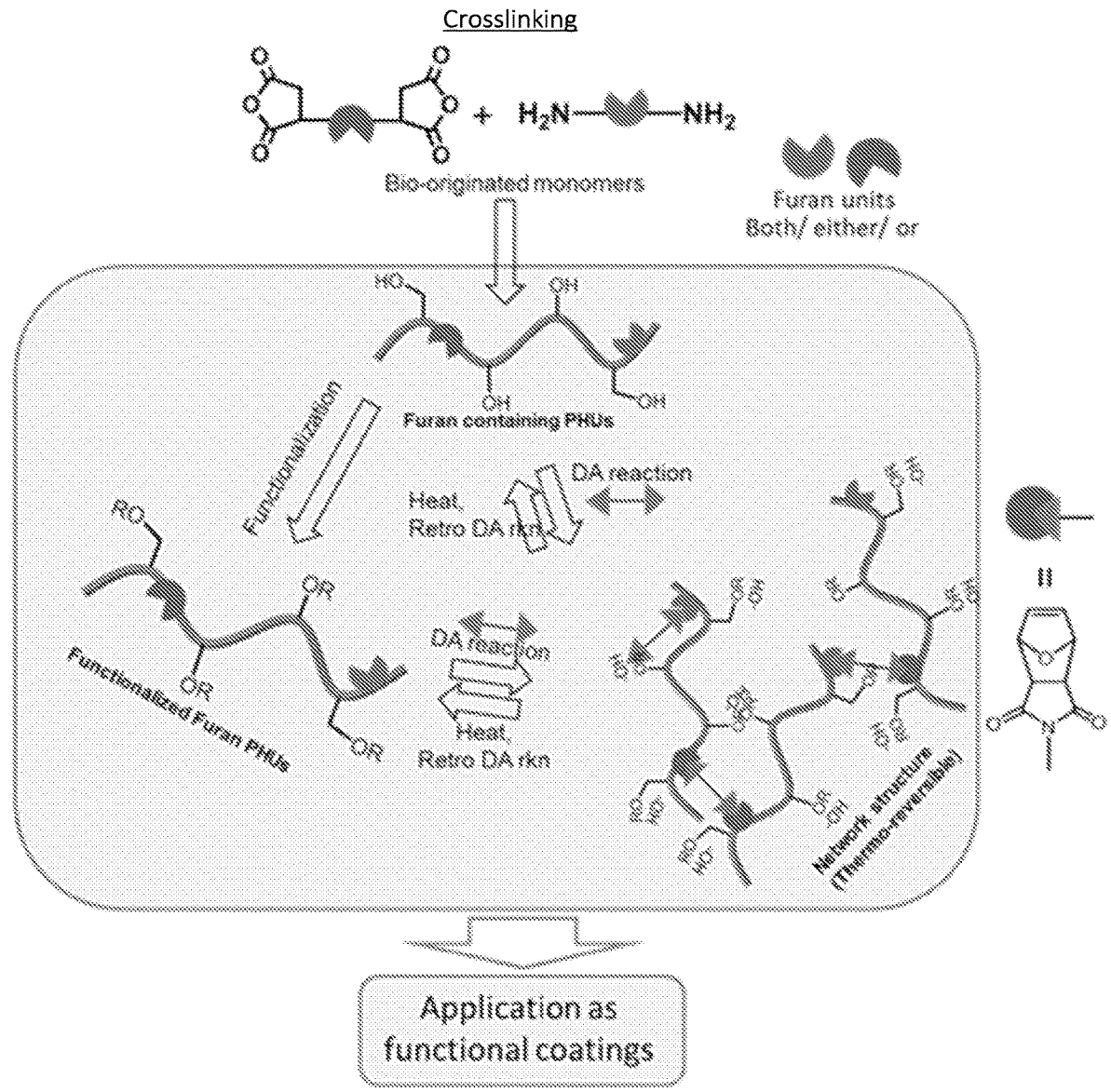
FIG. 11 provides a schematic of Scheme 2 which provides for a synthesis of furan containing PHUs/NIPUs from bio-originated monomers and their crosslinking.

Scheme 2, as provided and depicted in FIG. 11 provides the synthesis of furan containing PHUs/NIPUs from bio-originated monomers and their crosslinking. Scheme 2, as shown in FIG. 11, provides the synthesis of crosslinked PHUs/NIPUs from bio-originated monomers.

Figure 12:
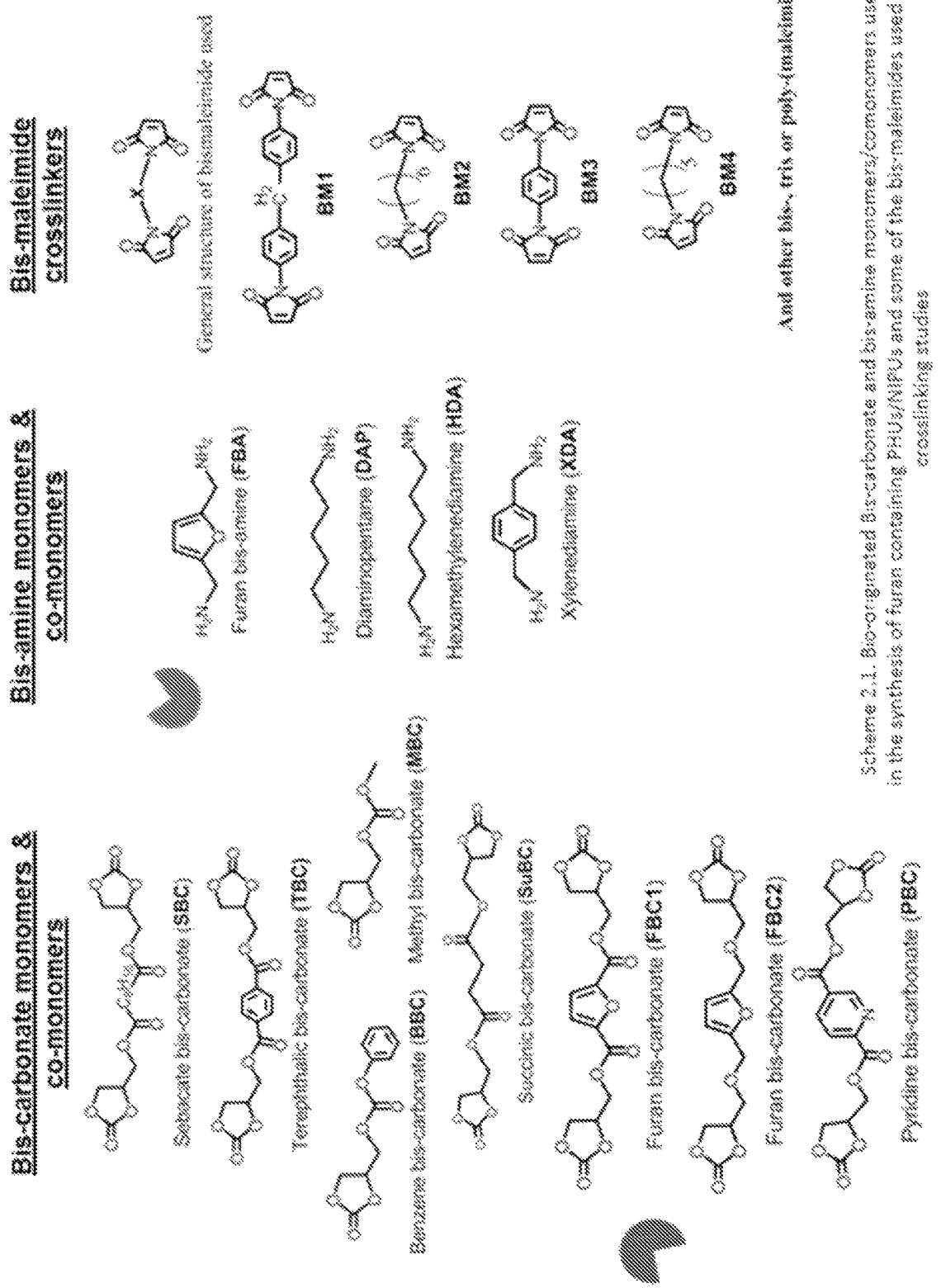
FIG. 12 provides a schematic of Scheme 2.1 which provides bio-originated bis-carbonate and bis-amine monomers used in the synthesis of furan containing PHUs/NIPUs and some of the bis-maleimides used for crosslinking studies.

Scheme 2.1, as provided for in FIG. 12, shows bio-originated bis-carbonate and bis-amine monomer/comonomers used in the synthesis of furan containing PHUs/NIPUs and come of the bis-maleimides used for crosslinking studies.

General Procedures for Synthesis, Purification, and Characterization of PHUs P1-P16

Using P16 as an example, the following describes the general procedures for synthesis, purification, and characterization of PHUs P1-P16.

For P16, FBC2 and 1,5-diaminopentane (DAP) were added into a reaction vial charged with a magnetic stirring bar. A few drops of mesitylene was added as internal reference. DMF was added and the reaction mixture was degassed with nitrogen for 15 minutes under stirring. The reaction mixture was stirred at 70° C. for 24 hours. The reaction mixture was added into diethyl ether to precipitate the polymer. The precipitated polymer was washed with diethyl ether for three times followed by drying at 60° C. under vacuum overnight. The polymer was taken for differential scanning calorimetry (DSC) and DMF gel permeation chromatography (GPC) analysis. Details are presented in Table 1.

Other polymers (P1-P15 in Table 1) were synthesized and characterized with similar methods. The active site for crosslinking site, i.e. the furan unit was introduced to the polymer by judicious selection of furan containing bis-carbonate or furan containing bis-amine monomers or both (Schemes 2 and 2.1).

The details of the polymerization conditions and GPC data of the polyhydroxyurethanes P1 to P16 synthesized according to the method described in Scheme 2 are provided in Table 1 as follows.

TABLE 1

Details of furan containing polyhydroxyurethanes (PHUs) P1 to P16 used for the examples

| PHU code | Bis-carbonate | Bis-amine | Monomer Conversion (%) | Yield (%) | Mn (g/mol) & PDI (DMF GPC) | Mn (g/mol) & PDI (LiBr/DMF GPC) | Glass transition temp., Tg (° C.) |
|---|---|---|---|---|---|---|---|
| P1 | SBC | FBA | 82.5 | N.A. | 5040; 1.56 | 6190; 1.67 | 10 |
| P2 | TBC | FBA | >90 | 85 | 4890; 2.21 | 3750, 1.99 | 51 |
| P3 | BBC | FBA | >90 | N.A. | 5220; 1.64 | 4560; 1.51 | 42 |
| P4 | MBC | FBA | >99 | 86 | N.A. | 2500; 1.51 | N.A. |
| P5 | MBC | FBA + HDA(1:3) | >99 | 73 | N.A. | N.A. | N.A. |
| P6 | FBC1 | FBA | >99 | N.A. | 3200; 1.31 | 3630, 1 41 | 19 |
| P7 | FBC2 | FBA | >95 | N.A. | 2670; 1.49 | 3440, 1 45 | 14 |
| P8 | FBC1 | DAP | >92 | 53 | 3920; 1.37 | 4680; 1.55 | 22 |
| P9 | FBC2 | DAP | >99 | 77 | 3410; 1.85 | 4320; 2.04 | −3 |
| P10 | FBC1 | XDA | >81 | 49 | 2690; 1.35 | 2700, 1.68 | 51 |
| P11 | FBC2 | XDA | >59 | 54 | 2540; 1.74 | 2620, 1.70 | −1 |
| P12 | FBC1 | HDA | >99 | 61 | N.A. | 4760, 1.50 | 19 |
| P13 | FBC2 | HDA | >98 | 65 | N.A. | 6980, 1.80 | −7 |
| P14 | PBC | FBA | >99 | 38 | 3020, 1.32 | 3100; 2.01 | N.A. |
| P15 | SuBC | FBA | 81 | 71 | 4350, 1.6 | — | 5 |
| P16 | FBC2 | DAP | >99 | 85 | 12700, 1.75 | — | 24.5 |

Scheme 3.1: Synthesis of Furan Containing PHUs/NIPUs (i.e. P1. P2. P3. P12) by Using Bis-Carbonate Monomers (i.e. SBC, TBC, BBC, and FBC1) and Bis-Amine Monomers (i.e. FBA and HDA)

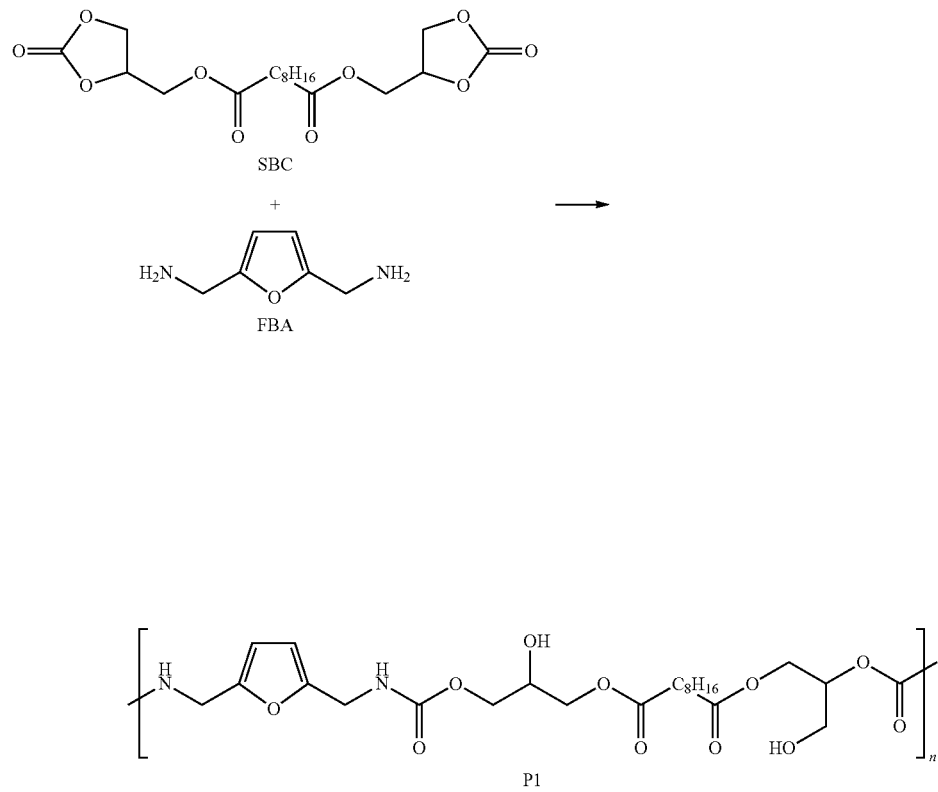

Scheme 3.1.
Synthesis of furan containing PHUs/NIPUs
(i.e. P1, P2, P3, P12)
by using bis-carbonate monomers
(i.e. SBC, TBC, BBC, and FBC1)
and bis-amine monomers (i.e. FBA and HDA)

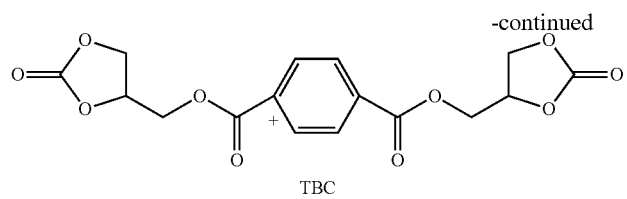
TBC
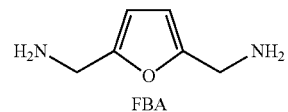
FBA
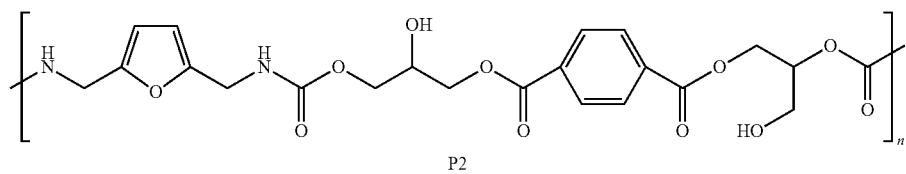
P2
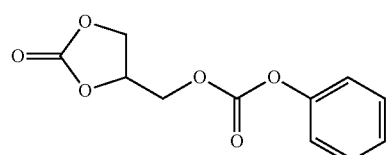
BBC
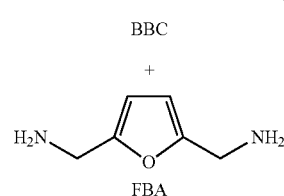
FBA
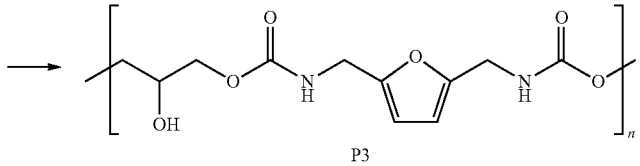
P3
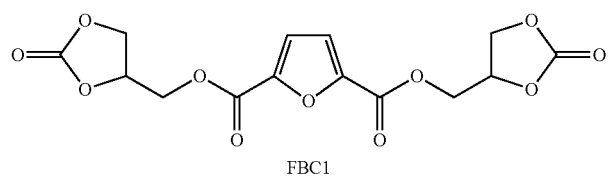
FBC1
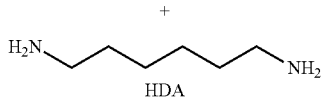
HDA
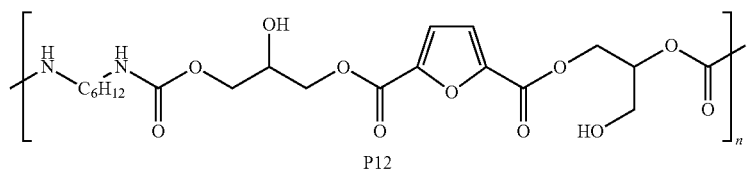
P12

Scheme 3.1 shows the synthetic procedures of some of the polyhydroxyurethanes described in Scheme 2. As shown in the scheme, polyhydrourethane P1 is synthesized by using SBC as the bis-carbonate monomer and FBA as the bis-amine monomer. Polyhydrourethane P2 is synthesized by using TBC as the bis-carbonate monomer and FBA as the bis-amine monomer. Polyhydrourethane P3 is synthesized by using BBC as the bis-carbonate monomer and FBA as the bis-amine monomer. Polyhydrourethane P12 is synthesized by using FBC1 as the bis-carbonate monomer and HDA as the bis-amine monomer.

Scheme 3.2: Synthesis of Polyhydrourethane P2 Starting From a Precursor Compound (i.e. Terephthalic Acid (TPA)) Derived From a Bio-based Source Scheme 3.2.
Synthesis of polyhydrourethane P2 starting from a precursor compound (i.e. terephthalic acid (TPA)) derived from a bio-based source

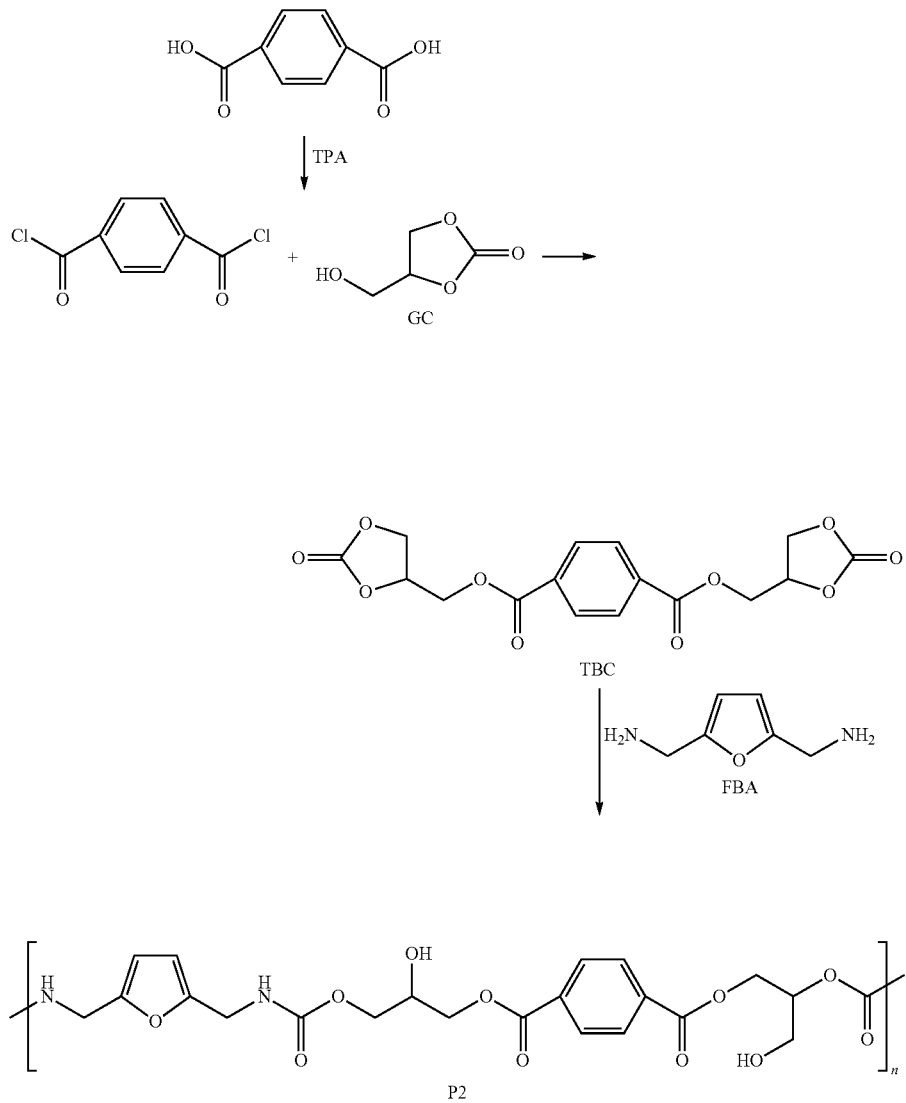

Polyhydrourethane P2 is synthesized by using TBC as the bis-carbonate monomer and FBA as the bis-amine monomer. As shown in Scheme 3.2, TBC is synthesized from a precursor compound, i.e. terephthalic acid (TPA) derived from a bio-based source.

Scheme 3.3: Synthesis of Polyhydrourethane P3 Starting from Phenyl Chloroformate (PCF) and Glycerol Carbonate (GC) as Starting Materials Scheme 3.3.
Synthesis of polyhydrourethane P3 starting from phenyl chloroformate (PCF) and glycerol carbonate (GC) as starting materials

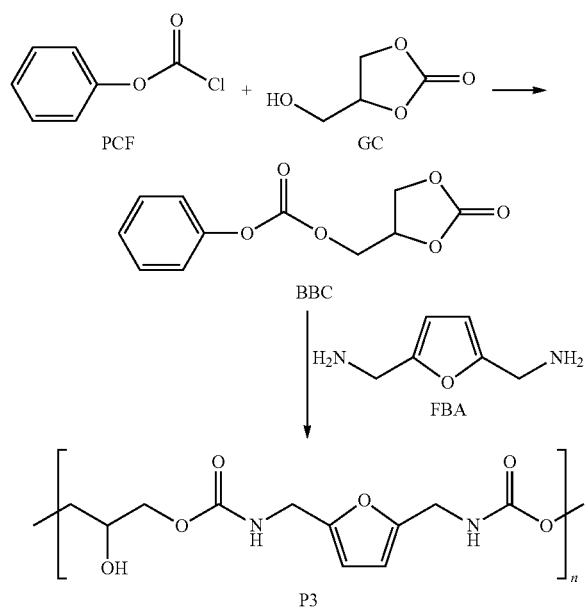

Polyhydrourethane P3 is synthesized by using BBC as the bis-carbonate monomer and FBA as the bis-amine monomer. As shown in Scheme 3.3, BBC is synthesized from phenyl chloroformate (PCF) and glycerol carbonate (GC).

Scheme 3.4.
Synthesis of polyhydrourethane P12 starting from glycerol carbonate (GC) and a precursor compound (i.e. furan-2,5-dicarboxylic acid (FDCA)) derived from bio-based source

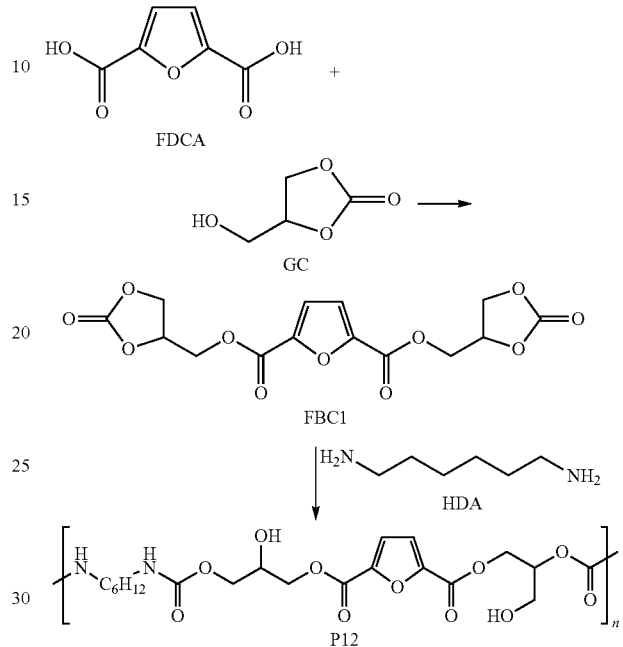

Polyhydrourethane P12 is synthesized by using FBC1 as the bis-carbonate monomer and HDA as the bis-amine monomer. As shown in Scheme 3.4, FBC1 is synthesized from glycerol carbonate (GC) and a precursor compound (furan-2,5-dicarboxylic acid (FDCA)) derived from a bio-based source.

Figure 13:
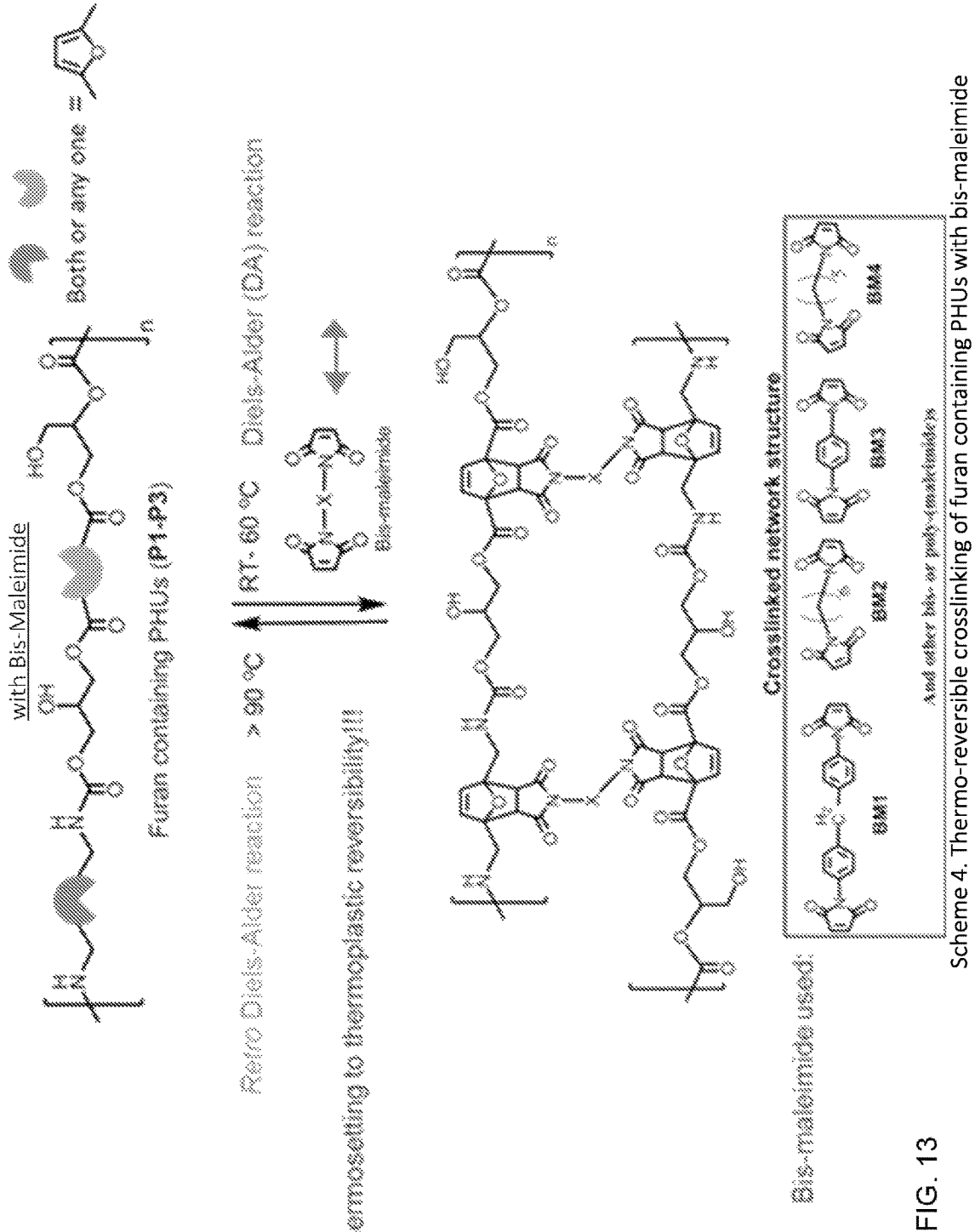
FIG. 13 provides a schematic of Scheme 4 which provides a thermo-reversible crosslinking of furan containing polyhydroxyurethanes (PHUs)/Non-Isocyanate Polyurethanes (NIPUs) with bis-maleimide.

Scheme 4, as shown in FIG. 13, provides a thermo-reversible crosslinking of furan containing polyhydroxyurethanes (PHUs)/non-isocyanate polyurethanes (NIPUs) with bis-maleimide. Thus, FIG. 13, shows Scheme 4, which provides thermo-reversible crosslinking of furan containing PHUs with bis-maleimide.

Scheme 5. Crosslinking of PHUs/NIPUs (Prepared from Polymerisation of FBC2 and DAP) with BM1 as the Crosslinking Agent Scheme 5.
Crosslinking of PHUs/NIPUs (prepared from polymerisation of FBC2 and DAP) with BM1 as the crosslinking agent

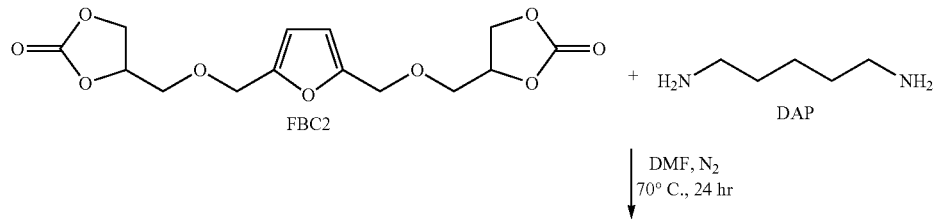

DMF, N$_2$
70° C., 24 hr

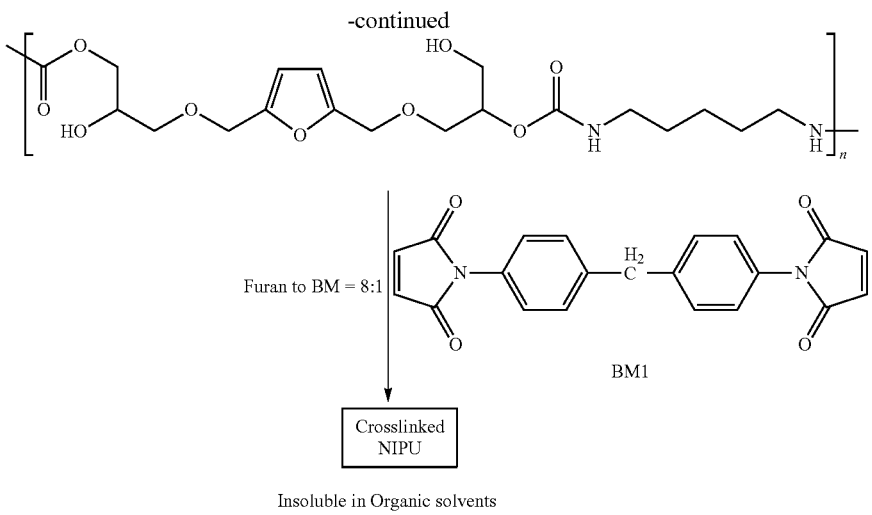

Crosslinking Behavior and Evaluation of Materials Properties

Unless otherwise stated, the crosslinking procedures of the examples described below generally follow this method:

The polymer (for e.g. P16) solution in DMF was added with bismaleimide ([Furan]:[BM1]=1:0.25). The reaction mixture was mixed and sonicated for at least 10 minutes to give a homogenous solution. The resulting viscous polymer solution was immediately used for further studies.

Example 1

Crosslinking reactions were performed on polymers PHU1 (i.e. P1 obtained from the polymerisation of SBC and FBA according to Table 1), PHU2 (i.e. P2 obtained from the polymerisation of TBC and FBA according to Table 1), PHU3 (i.e. P3 obtained from the polymerisation of BBC and FBA according to Table 1) and PHU4 (i.e. P6 obtained from the polymerisation of FBC1 and FBA according to Table 1) using BM1, BM2 or BM3 as the crosslinking agent in varying molar ratios (i.e. 1:0.25, 1:0.5 or 1:1). The results on the gel formation are provided in the table below.

TABLE 2

Gel formation of the crosslinked PHUs/NIPUs via Diels-Alder Reaction

| No. | Polymer | Bis-maleimide | Polymer:BM | Gel at RT (Overnight) | Gel at 50° C. (Overnight) | Comments |
|---|---|---|---|---|---|---|
| 1 | P1 | BM1 | 1:1 | No | No | Gel on storage!! |
| 2 | P2 | BM1 | 1:1 | No | Yes | |
| 3 | P3 | BM1 | 1:1 | Yes | | |
| 4 | P3 | BM1 | 1:0.5 | yes | | |
| 5 | P3 | BM1 | 1:0.25 | No | Yes | |
| 6 | P3 | BM2 | 1:0.5 | Yes | | |
| 7 | P3 | BM3 | 1:0.5 | No | Yes | |

100 mg of polymer in 1 ml of DMF

Example 2

Crosslinking PHUs and Film Formation Studies (Formation of Organo-Gel)

Crosslinking reactions were performed on polymer P3 (obtained from the polymerisation of BBC and FBA) using 1,1'-(Methylenedi-4,1-phenylene)bismaleimide (BM1) as the crosslinking agent. The experiments were performed under two different reaction conditions: (i) P3 and BM1 were mixed in a molar ratio of 1:0.5 at room temperature and allowed to crosslink overnight and (ii) P3 and BM1 were mixed in a molar ratio of 1:0.25 at 50° C. for an hour. Both reaction conditions yielded a self-standing gel with a solid content of 16%, as shown in FIG. 1. The results show that bismaleimides crosslink furan containing NIPUs over a wide temperature range from room temperature to 50° C. Notably, a gel may be obtained from the viscous solution (i.e. reaction mixture) even at room temperature and without stirring after 24 hours.

Example 3

Coating on Different Substrates

Figure 2:
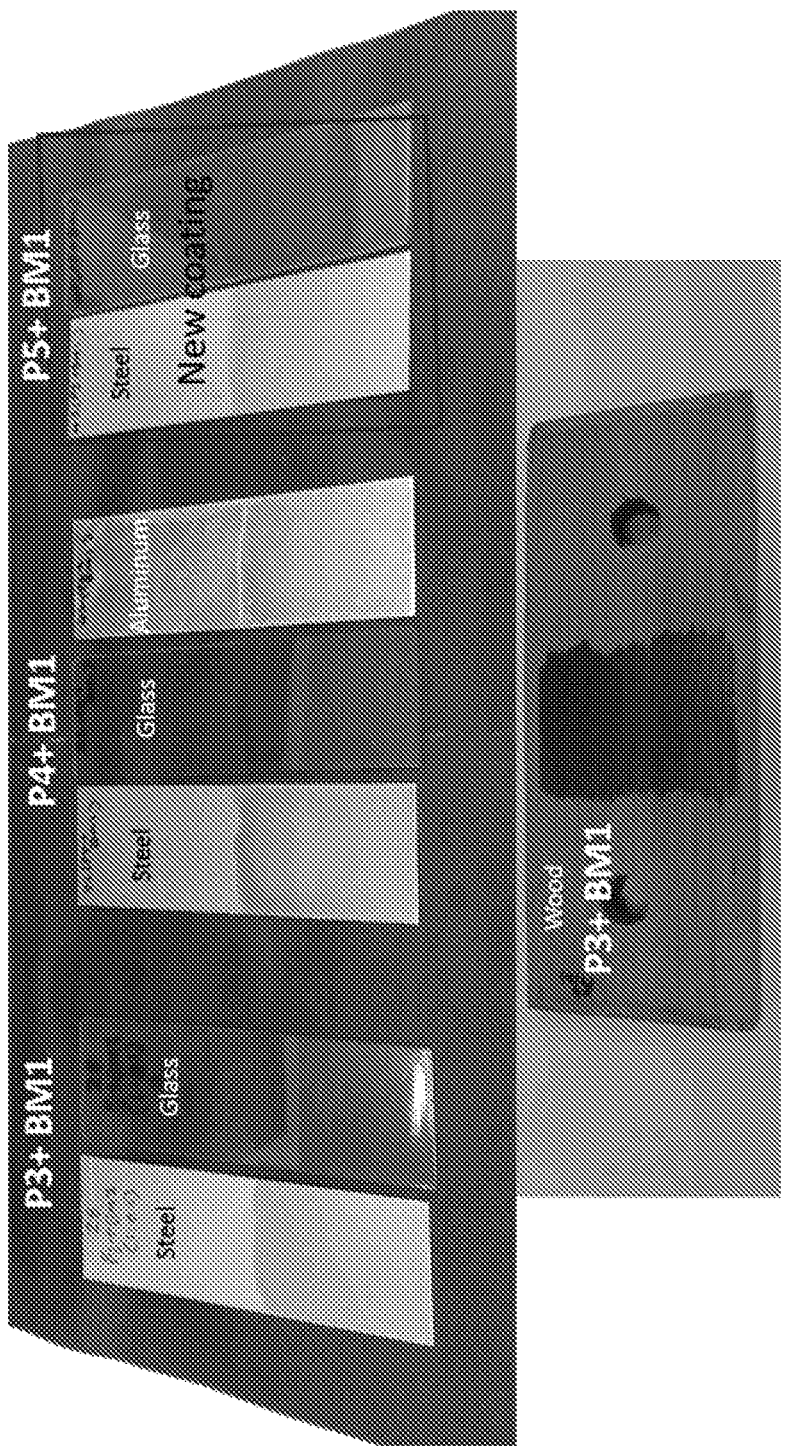
FIG. 2 shows images of crosslinked PHUs/NIPUs coatings in accordance with various embodiments disclosed herein. P3 crosslinked with BM1 was applied on steel, glass and wood substrates. P4 crosslinked with BM1 was applied on steel, glass and aluminum substrates. P5 crosslinked with BM1 was applied on steel and glass substrates.

Different substrates (glass, aluminum, steel and wood) were coated with polymers namely P3, P4, P5 and BM1 solution via a solvent casting method. The coated substrates were then dried in oven at 50° C. for 24 hours, followed by drying under vacuum at 50° C. for 48 hours (FIG. 2).

These results show that the crosslinked polymers according to embodiments disclosed herein are capable of being coated on a wide range of substrate surfaces.

Example 4

(a) Self-Standing Film

Figure 3B:
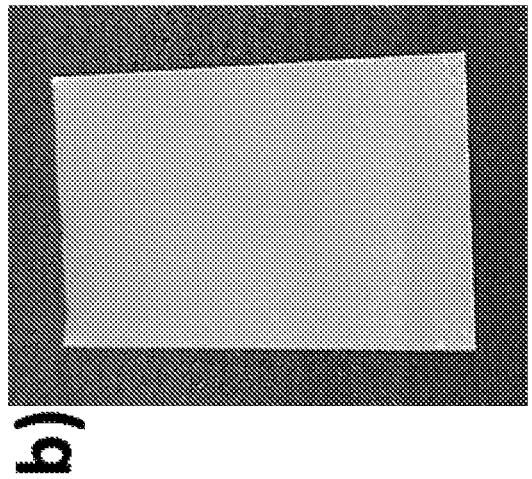
FIGS. 3A and 3B show images of crosslinked PHUs/NIPUs coatings in accordance with various embodiments disclosed herein.
Figure 3A:
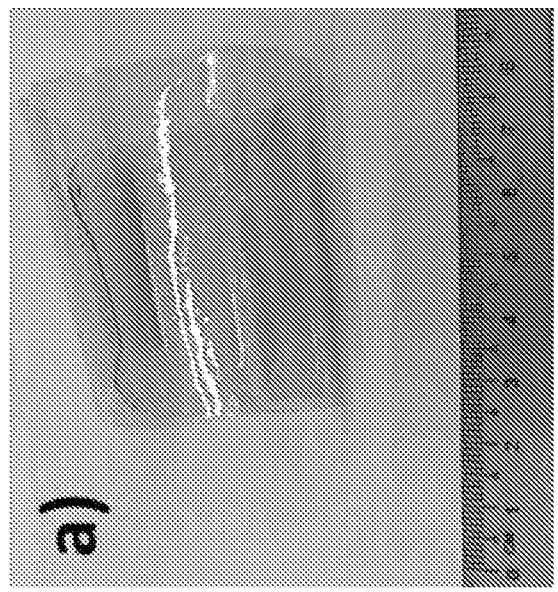

A cross-linked polymer (P16 crosslinked with BM1 in a molar ratio of 1:0.25) was coated on glass substrate using an applicator and then dried in oven at 50° C. for 24 hours, followed by drying under vacuum at 50° C. for 48 hours. The glass substrate was then submerged in ethanol for 15 minutes, followed by drying at ambient condition for 10 minutes. The polymer film was peeled off from glass substrate by using tweezer (FIG. 3A).

(b) Dip-Coating

A metal substrate was dip-coated with polymer solution (containing P16 and BM1 in a molar ratio of 1:0.25) in a small beaker. The coated metal substrate was dried in oven at 50° C. for 24 hours, followed by drying under vacuum at 50° C. for 48 hours (FIG. 3B).

Example 5

Water and Solvent Immersion Tests of Crosslinked PHU/NIPU Coatings

Figure 4:
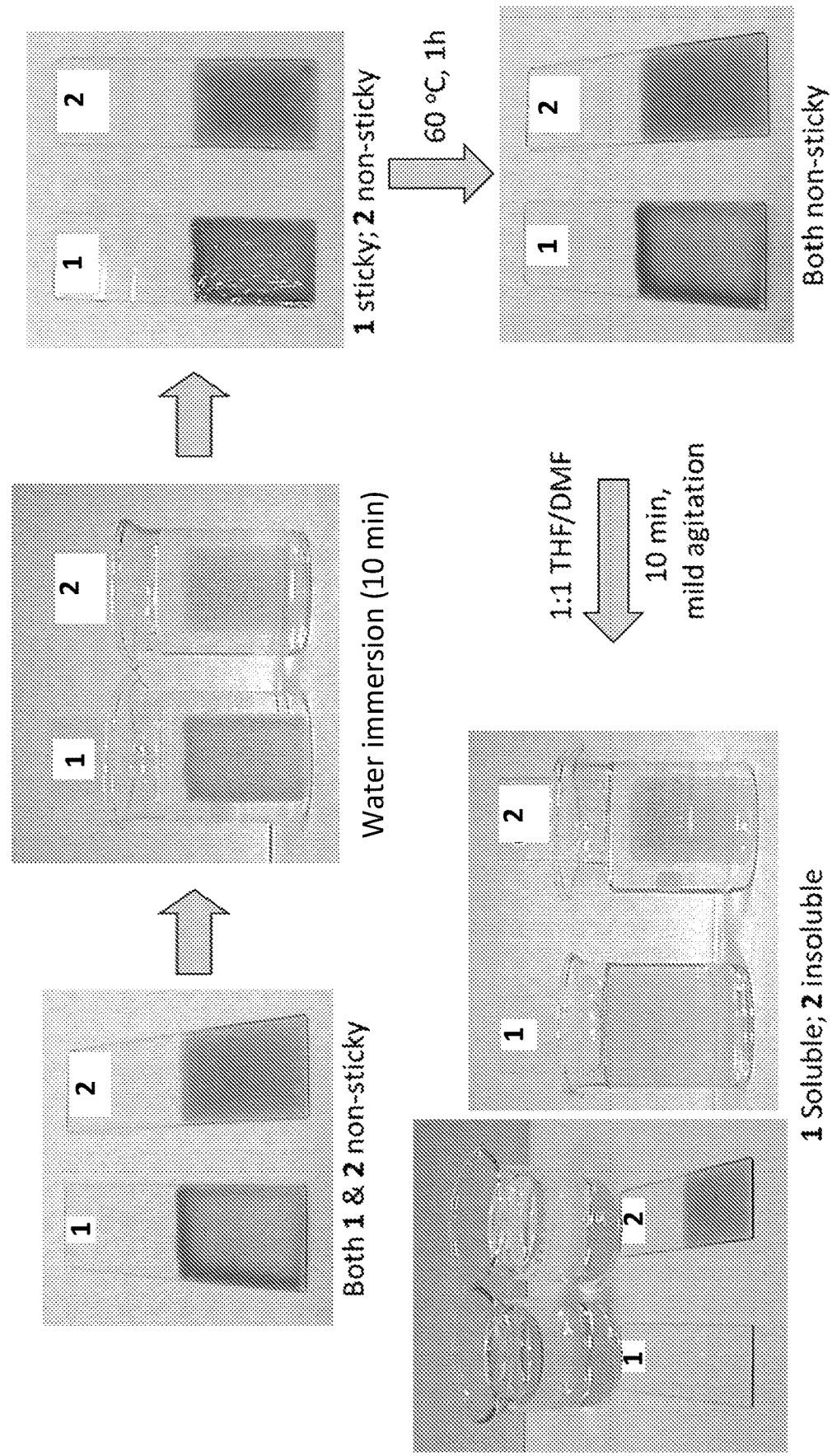
FIG. 4 shows images of crosslinked PHUs/NIPUs coatings in accordance with various embodiments disclosed herein. Un-crosslinked P3 coating (i.e. control) is shown on slide 1 and the coating formed from P3 crosslinked with BM1 in a molar ratio of 1:0.1 is shown on slide 2. The crosslinked PHUs/NIPUs coatings were immersed in water for 10 mins, heated at 60° C. for 1 hour and then immersed in a 1:1 mixture of DMF and THF with mild agitation for 10 mins. As shown, the crosslinked coating film (i.e. slide 2) has better solvent resistance properties than the non-crosslinked film (i.e. slide 1).

Coating films of polymer P3 were immersed in water and in organic solvent (1:1 DMF/THF) to test its water and solvent resistance properties before crosslinking (see slide 1) and after crosslinking (see slide 2). The control used was non-crosslinked P3 (i.e. slide 1). Two glass coupons coated with (i) P3 and (ii) P3 and BM1 in a molar ratio of 1:0.1 separately after complete drying were submerged in water for 10 min. The crosslinked coating showed significant reduction in water absorption and remained non-sticky (see FIG. 4, slide 2). Then the coupons were removed from the water and dried in an oven for a brief time (for e.g. heating at 60° C. for 1 hour). Next these coupons were immersed in 1:1 DMF/THF mixture with mild agitation for 10 mins. The BM1 crosslinked coating showed significantly reduced solubility in this organic solvent (see FIG. 4, slide 2). These results show that the crosslinked coating film (i.e. slide 2) has better solvent resistance properties than the non-crosslinked film (i.e. slide 1).

Example 6

Solubility and Recyclability Tests of Crosslinked PHU/NIPU Coatings

Figure 5:
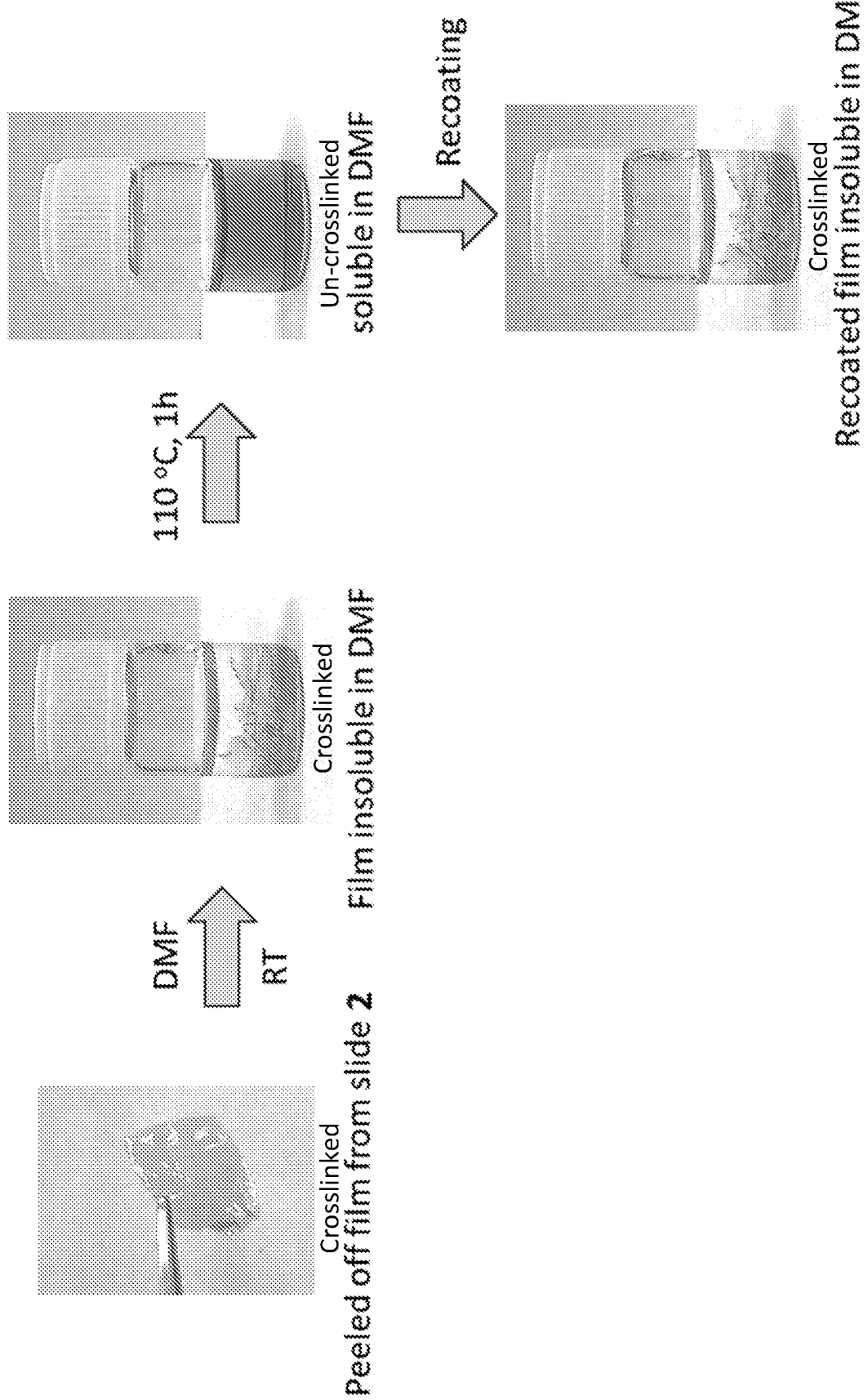
FIG. 5 shows images of crosslinked PHUs/NIPUs coatings in accordance with various embodiments disclosed herein. The crosslinked PHUs/NIPUs coatings were peeled off from slide 2 of FIG. 4 and were heated at 110° C. in DMF for 1 hour before being used to recoat slide 2. The recoated film on slide 2 was found to be insoluble in DMF. As shown, the crosslinked coating films can be recycled thermally by simply heating the films at elevated temperature and reused as a coating later without an appreciable loss in desired properties e.g. solvent resistance.

Images obtained from experiments conducted on crosslinked PHU/NIPU coatings to test for their solubility and recycling properties are provided in FIG. 5. The crosslinked PHU/NIPU coating (obtained from the crosslinking of P3 with BM1 in a molar ratio of 1:0.1) was peeled off from slide 2. The self-standing crosslinked film produced using polymer P3 and BM1 after drying was submerged in DMF for 24 hours. The film did not dissolve. However, when the solution was heated to 110° C. for 60 minutes, the crosslinked film dissolved due to the retro Diels-Alder (rDA) reaction. The resulting polymer solution was drop casted on a glass substrate to form a re-crosslinked film upon drying (FIG. 5) and interestingly, the recoated film was insoluble in DMF. Interestingly, it has been shown that the crosslinked coating films can be recycled thermally by simply heating the films at elevated temperature.

Example 7

Pencil Hardness Test

The pencil hardness test (ASTM D3363) was carried out on the polymer coated steel substrate (prepared according to the methods used in Example 3) with Elcometer 501 Pencil Hardness Tester and pencils (grades 6B-6H). The pencil hardness that did not cut or scratch the coating was recorded. The test was repeated for two times on different areas of the coating. The results are recorded in Table 3.

TABLE 3

Degree of crosslinking and crosslinking density and pencil hardness data of crosslinked PHU/NIPU films

| Sample | Polymer used for coating | Bis-maleimide (BM) used for cross-linking | Polymer [(Furan)]:BM | DMF used mixing polymer and BM | Degree of cross linking (%) | Cross-linking density$^c$ (mmol/cm$^3$) | Pencil hardness of cross-linked dry film | Remarks |
|---|---|---|---|---|---|---|---|---|
| S1 | P16 | BM2 | 1:0.15 | 0.25 mL | 15$^b$ | 0.6 | 4B | — |
| S2 | P16 | BM2 | 1:0.25 | 0.25 mL | 29$^a$ | 1.0 | 3B | — |
| S3 | P16 | BM2 | 1:0.35 | 0.30 mL | 35$^b$ | 1.4 | 3B | — |
| S4 | P16 | BM2 | 1:0.50 | 0.35 mL | 53$^a$ | 2.0 | 3B | BM precipitation |
| S5 | P16 | BM1 | 1:0.15 | 0.25 mL | 15$^b$ | 0.6 | 3B | — |
| S6 | P16 | BM1 | 1:0.25 | 0.25 mL | 25$^b$ | 1.0 | 2B | — |
| S7 | P16 | BM1 | 1:0.35 | 0.30 mL | 35$^b$ | 1.4 | 2B | — |
| S8 | P16 | BM1 | 1:0.50 | 0.45 mL | 50$^b$ | 2.0 | 3B | — |

TABLE 3-continued

Degree of crosslinking and crosslinking density and pencil hardness data of crosslinked PHU/NIPU films

| Sample | Polymer used for coating | Bis-maleimide (BM) used for cross-linking | Polymer [(Furan)]:BM | DMF used mixing polymer and BM | Degree of cross linking (%) | Cross-linking density$^c$ (mmol/cm$^3$) | Pencil hardness of cross-linked dry film | Remarks |
|---|---|---|---|---|---|---|---|---|
| S9 | P16 | None | None | 0.25 mL | None | None | Softer than 6B | Sticky film |
| S10 | P3 | BM1 | 1:0.05 | 0.25 mL | 5$^b$ | 0.2 | N.A. | — |

$^a$= observed from $^1$H NMR; $^b$= calculated considering ~50% crosslinking efficiency; $^c$= calculated from equation v = 2p/(Mc), where v is crosslink density, p is density of crosslinked polymer, and Mc is average molecular weight between crosslink point.
The polymer-BM solution in DMF was heated at 50° C. for 10 minutes to ensure full dissolution of BM. The polymer-BM solution was cooled to room temperature and coated on steel coupon, followed by drying at 50° C. for 24 hours.

Example 8

Thermo-healing and Self-healing Properties of Crosslinked PHU/NIPU Coatings

Figure 6:
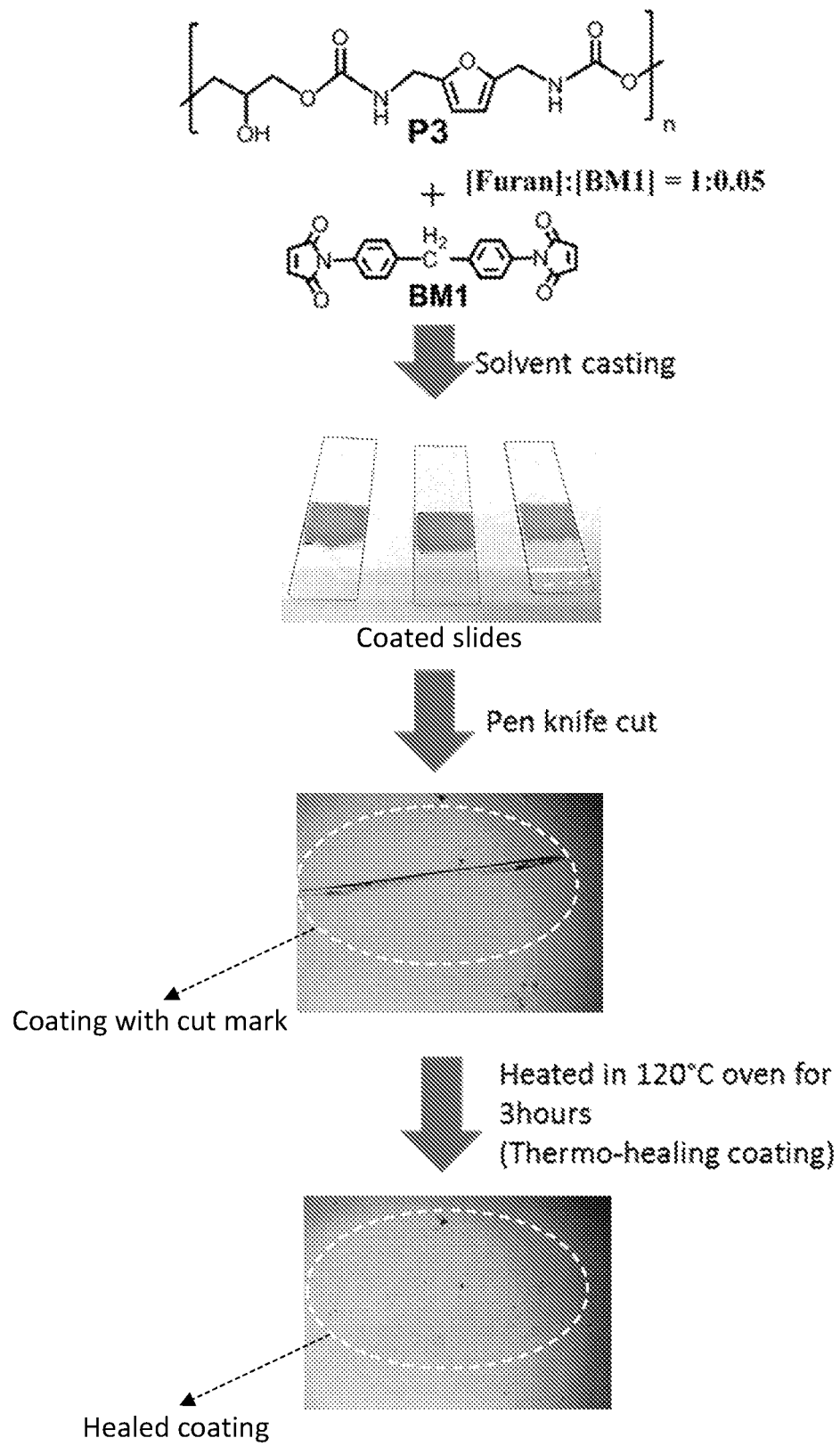
FIG. 6 shows images of crosslinked PHUs/NIPUs coatings in accordance with various embodiments disclosed herein. The crosslinked PHUs/NIPUs coating was formed by adding P3 to bismaleimide BM1 in the molar ratio of 1:0.05 in the presence of DMF before casting on a glass slide and dried at room temperature. The crosslinked PHUs/NIPUs coatings were then cut using a pen knife and then heated at 120° C. in the oven for 3 hours. As shown, the crosslinked coating film can be healed completely by simply heating the films at elevated temperature.
Figure 7:
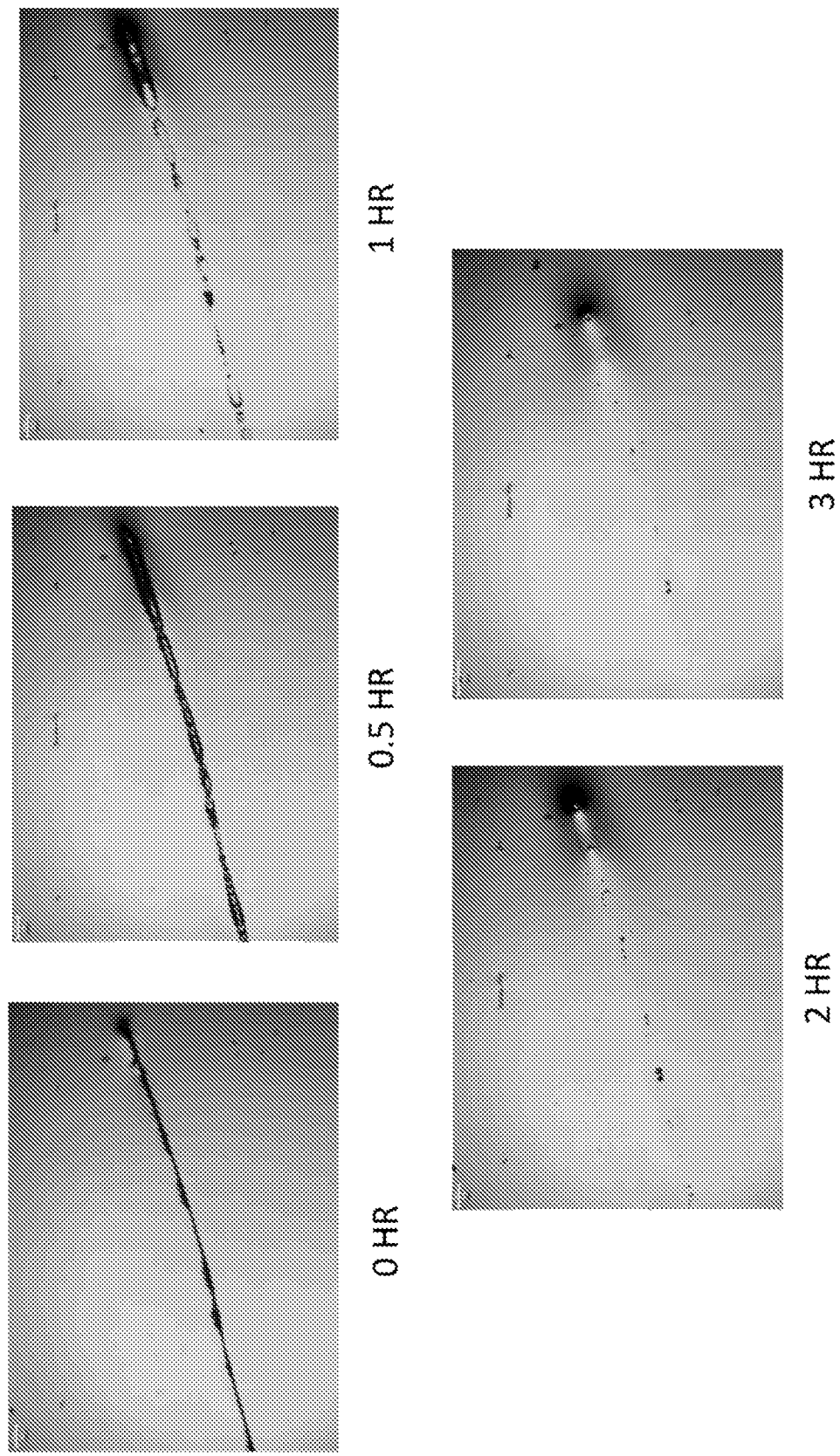
FIG. 7 shows images of the transient states of the cut crosslinked PHUs/NIPUs coatings of FIG. 6 after being heated for 0.5 hour, 1 hour, 2 hours and 3 hours.
Figure 8:
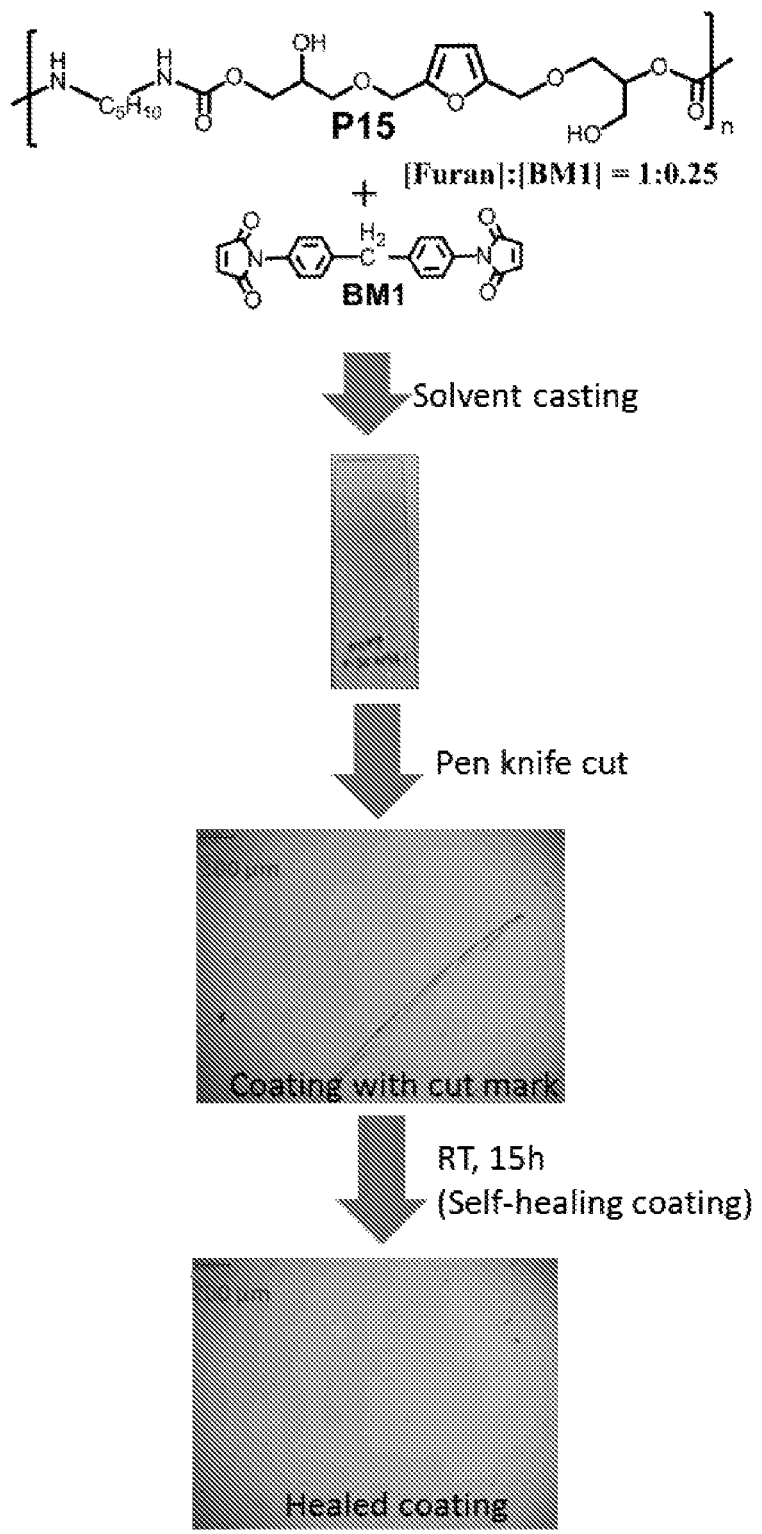
FIG. 8 shows images of crosslinked PHUs/NIPUs coatings in accordance with various embodiments disclosed herein. The crosslinked PHUs/NIPUs coating was formed by adding P15 to bismaleimide BM1 in the molar ratio of 1:0.25 in the presence of DMF before casting on a glass slide and dried at room temperature. The crosslinked PHUs/NIPUs coatings were then cut using a pen knife and then dried at room temperature for 15 hours. As shown, the crosslinked coating film can be healed completely by simply drying the films at room temperature.

Images obtained from experiments conducted on crosslinked PHU/NIPU coatings to test for their healing properties are provided in FIGS. 6 to 8. In these experiments, the self-standing crosslinked coating films were scratched by using a pen knife. The polymer film was placed under different conditions, such as in the desiccator, ambient condition, or elevated temperature (>100° C.) to test their healing property. The thermo- or self-healing of scratch on the film was recorded by microscope over 24 hours.

(a) Crosslinked PHU/NIPU of Polymer P3 with BM1 (Thermo-Healing)

P3 with bismaleimide BM1 in a molar ratio of 1:0.05 in DMF solution was casted on a glass slide and dried at room temperature. A cut was created on the coating using a pen knife as shown in the micrograph in FIG. 6. After heating at 120° C. in the oven for 3 hours, the micrograph showed complete thermo-healing of the coating. As shown, the crosslinked coating film can be healed completely by simply heating the films at elevated temperature.

A second experiment was conducted to monitor the healing process of the coating over 3 hours of heating. The transient states of the coating after being heated for 0.5 hour, 1 hour, 2 hours and 3 hours are provided in FIG. 7.

(b) Crosslinked PHU/NIPU of Polymer P15 with BM1 (Self-Healing)

P15 with bismaleimide BM1 in a molar ratio of 1:0.25 in DMF solution was casted on a glass slide and dried at room temperature. A cut was created on the coating using a pen knife as shown in the micrograph in FIG. 8. After drying for 15 hours at room temperature, the micrograph showed complete self-healing of the coating. As shown, the crosslinked coating film can be healed completely by simply drying the films at room temperature.

These results show that the crosslinked polymers according to embodiments disclosed herein are capable of being used in applications where thermo healing/self healing properties are required/beneficial (e.g. without the addition of any external chemical reagents).

Example 9

Shape-Memory Properties of Crosslinked PHU/NIPU Coatings

Figure 9:
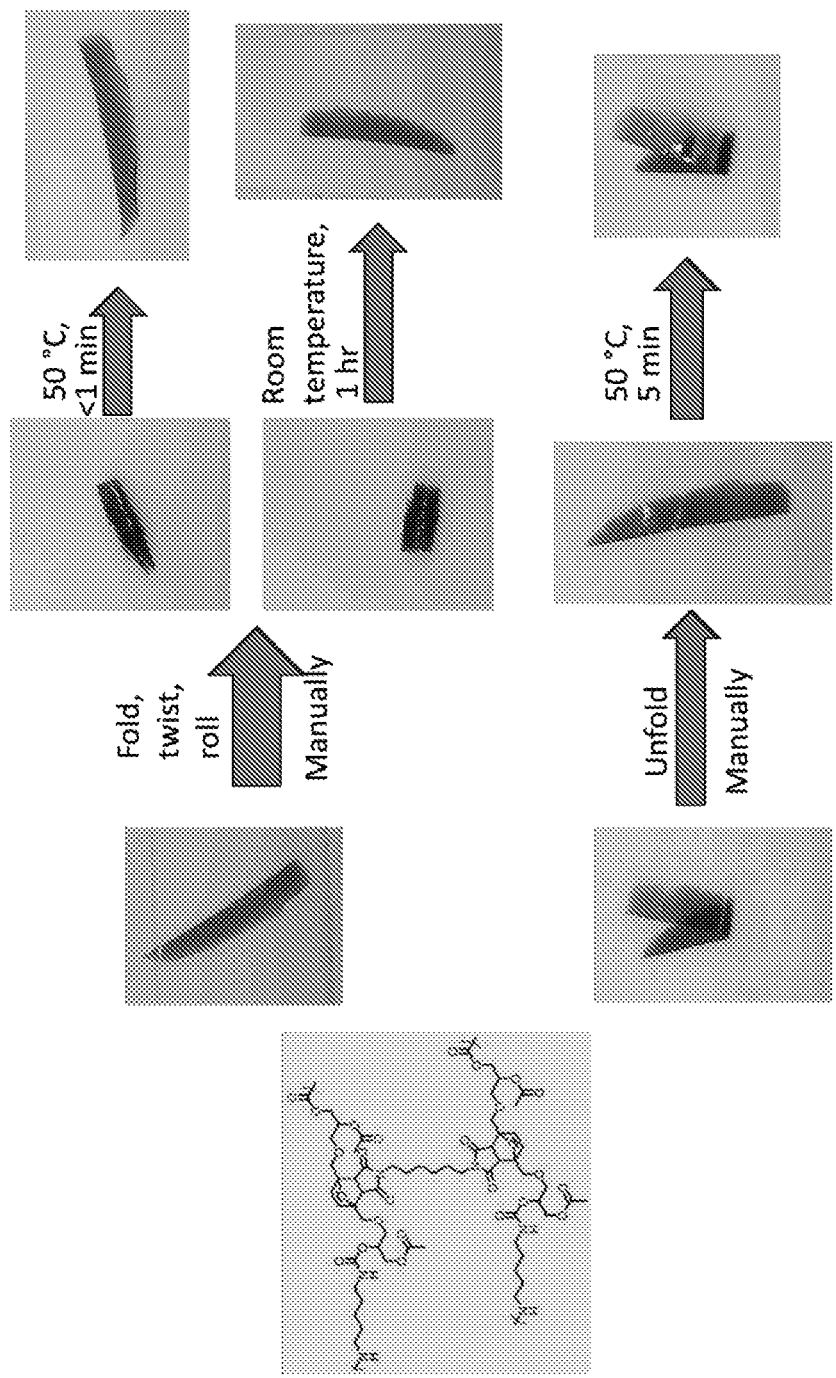
FIG. 9 shows images of crosslinked PHUs/NIPUs coatings in accordance with various embodiments disclosed herein. The self-standing crosslinked coating film was folded, twisted and rolled manually. As shown, the distorted film returned to its original shape in about 1 hour at room temperature or after simply heating the film at 50° C. for less than 1 min. In another example, the flat film was heated at 120° C. for 4 hours and subsequently folded, followed by heating at 50° C. overnight to set a permanent folded shape. The folded film was then unfolded manually to a flattened flim. As shown, the flattened film returned to its folded shape after simply heating at 50° C. for 5 mins.
Figure 10:
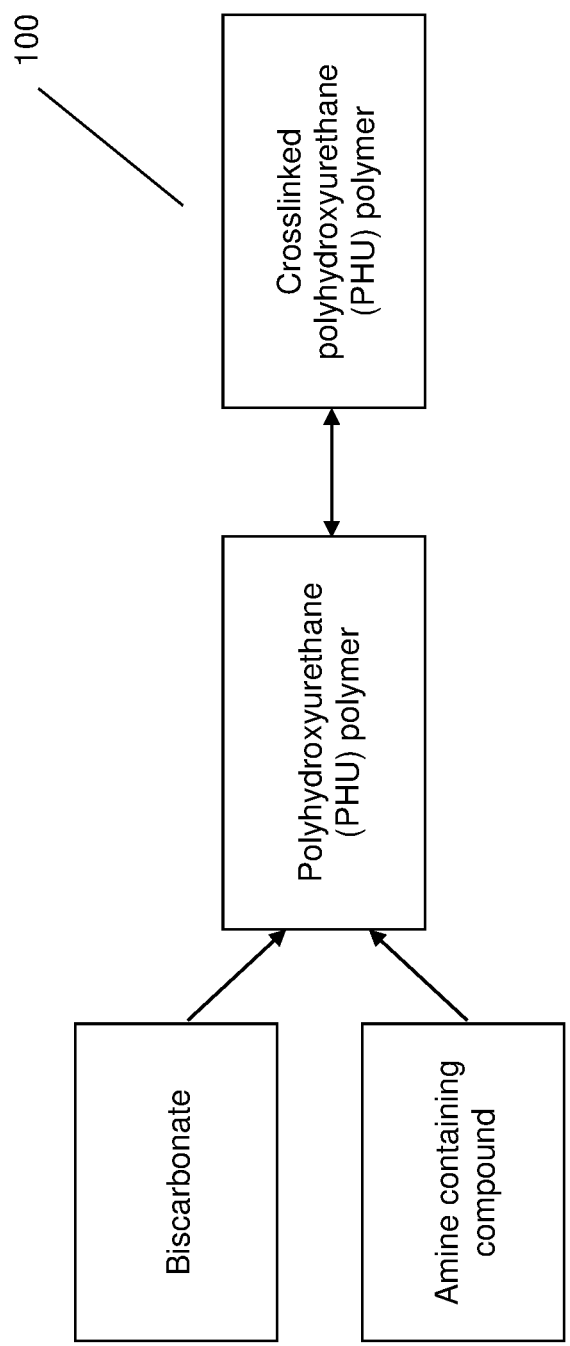
FIG. 10 is a schematic flowchart 100 for illustrating a method of preparing a crosslinked polyhydroxyurethane (PHU) polymer in accordance with various embodiments disclosed herein. In various embodiments, the conversion from a PHU polymer into its crosslinked PHU polymer is reversible. In various embodiments, the PHU polymer is obtained from the reaction between a biscarbonate that is optionally derived from a bio-based source and an amine containing compound that is optionally derived from a bio-based source.

The self-standing crosslinked coating film (from Example 3) was folded, twisted and rolled by using a tweezer at room temperature. The distorted film was heated to 50° C. in oven for less than about 1 min to recover to its original shape (FIG. 9). The folded film was also unfolded at room temperature in about 1 hour.

In another example, the flat film was heated at 120° C. for 4 hours and subsequently folded, followed by heating at 50° C. overnight to set the permanent folded shape. The folded film was then unfolded at room temperature. The flattened film recovered to its folded shape upon heating at 50° C. for about 5 mins (FIG. 9).

These results show that the crosslinked polymers according to embodiments disclosed herein are capable of being used in applications where shape memory properties are required/beneficial.

In summary, the examples provided above collectively report crosslinking of PHUs with diene moieties in the back bone synthesized using bio-originated monomers via Diels-Alder (DA) reaction. Coatings obtained in the examples are suitable for diverse range of substrates including glass, metal (Al/steel), plastic and wood. These exemplary crosslinked coating films were proved to have tunable hardness and improved water and solvent resistance properties. These exemplary crosslinked coating films can be recycled thermally via retro Diels-Alder reaction by simply heating the films at elevated temperature and the coatings are reported to have self- or thermo-healing and shape-memory properties.

Applications

Various embodiments of the present disclosure provide a green and sustainable strategy to obtain a polyhydroxyurethane polymer and a crosslinked polyhydroxyurethane polymer from a bio-based source. In various embodiments of the methods disclosed herein, the process does not involve the use of toxic isocyanates and phosgene, thereby making the production process friendly to the environment.

Various embodiments of the present disclosure also provides crosslinked PHU polymers that are recyclable, i.e. they have thermo-reversible or thermally reversible crosslink networks and can be easily converted from a thermosetting polymer to their thermoplastic precursors by a simple heat application. In various embodiments, the crosslinked polymer disclosed herein has self healing/thermo healing properties and also show good resistance towards polar (for e.g. water) and non-polar solvents (for e.g. organic solvents). In various embodiments therefore, the crosslinked PHU polymers disclosed herein may be in the form of a new emerging class of polyurethanes that can be used in a wide array of application such as serving as resins for solvent-borne coatings on a wide range of substrates (such as glass, metal, plastic, fabric or wooden substrates), as thermally removable coatings for electronic applications, as self-healing or thermo-healing coatings and also in the manufacturing of hot melt adhesives. The present disclosure has demonstrated the principles involved, and opens the way for further scale-up in many applications.

It will be appreciated by a person skilled in the art that other variations and/or modifications may be made to the embodiments disclosed herein without departing from the spirit or scope of the disclosure as broadly described. For example, in the description herein, features of different exemplary embodiments may be mixed, combined, interchanged, incorporated, adopted, modified, included etc. or the like across different exemplary embodiments. The present embodiments are, therefore, to be considered in all respects to be illustrative and not restrictive.

The invention claimed is:

1. A method of crosslinking a polyhydroxyurethane (PHU) polymer having a plurality of diene moieties in the backbone, the method comprising:
reacting a crosslinking agent having two or more dienophile moieties with the PHU polymer backbone to form crosslinks between the diene moieties via a plurality of diene-dienophile adducts,
wherein at least a part of the diene-dienophile adduct comprises structure (I):

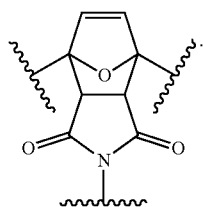

Structure (I)

2. The method according to claim 1, wherein the crosslinking occurs below a threshold temperature beyond which crosslinks are removed from the PHU polymer.

3. The method according to claim 1, wherein the crosslinking is carried out at ambient room temperature or above.

4. The method according to claim 1, wherein the diene moiety comprises a furan moiety.

5. The method according to claim 1, wherein the dienophile moiety comprises a maleimide moiety.

6. The method according to claim 1, wherein the crosslinking agent is a bismaleimide.

7. The method according to claim 6, wherein the bismaleimide is selected from the group consisting of 1,1'-(Methylenedi-4,1-phenylene)bismaleimide (BM1), N,N'-hexamethylenebismaleimide, (BM2), N,N'-(1,4-Phenylene) dimaleimide (BM3) and N,N'-pentamethylenebismaleimide (BM4).

8. The method according to claim 1, wherein the PHU polymer and the crosslinking agent are reacted in a molar ratio of 1:0.05-1.

9. The method according to claim 1, further comprising, reacting at least one biscarbonate with at least one amine containing compound to form the PHU polymer, prior to reacting the PHU polymer with the crosslinking agent,
wherein at least one of the biscarbonate or amine containing compound comprises a diene moiety.

10. The method according to claim 9, wherein the biscarbonate is selected from the group consisting of sebacate bis-carbonate (SBC), terephthalic bis-carbonate (TBC), benzene bis-carbonate (BBC), methyl bis-carbonate (MBC), succinic bis-carbonate (SuBC), bis((2-oxo-1,3-dioxolan-4-yl)methyl)furan-2,5-dicarboxylate (FBC1), 4,4'-(((furan-2,5-diylbis(methylene))bis(oxy))bis(methylene))bis(1,3-dioxolan-2-one) (FBC2), bis((2-oxo-1,3-dioxolan-4-yl) methyl)pyridine-2,5-dicarboxylate (PBC), bis((2-oxo-1,3-dioxolan-4-yl)methyl)pyridine-2,6-dicarboxylate (PBC-2) and 4,4'-(((tetrahydrofuran-3,4-diyl)bis(oxy))bis(methylene))bis(1,3-dioxolan-2-one) (HFBC), and the amine containing compound is selected from the group consisting of furan bis-amine (FBA), xylene diamine (XDA), diaminopentane (DAP) and hexamethylenediamine (HDA).

11. The method according to claim 9, wherein the biscarbonate is prepared from a bio-based source and/or the amine containing compound is prepared from a bio-based source.

12. The method according to claim 1, further comprising, functionalizing the PHU polymer with one or more substituents selected from the group consisting of alkyl, sulfate, sulfonate, phosphate, carboxylate, sulfobetaine, phosphobetaine, cinnamate, fatty acid, amino acid, lactic acid, polylactic acid, caprolactone, polycaprolactone, polysiloxane and combinations thereof to form a functionalized PHU polymer, prior to reacting said PHU polymer with the crosslinking agent.

13. A crosslinked polyhydroxyurethane (PHU) polymer obtained from reacting a crosslinking agent having two or more dienophile moieties with the PHU polymer backbone to form crosslinks between the diene moieties, the crosslinked polymer comprising a plurality of diene-dienophile adducts, wherein at least a part of the diene-dienophile adduct comprises structure (I):

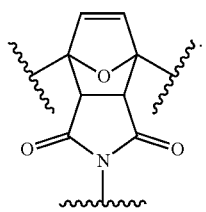

Structure (I)

14. The crosslinked polymer according to claim 13, wherein the diene-dienophile adduct is formed from a Diels-Alder reaction between the diene moiety and the dienophile moiety.

15. The crosslinked polymer according to claim 13, wherein the diene moiety comprises furan and/or the dienophile moiety comprises maleimide.

16. The crosslinked polymer according to claim 13, wherein the crosslinking agent is a bismaleimide represented by general formula (I):

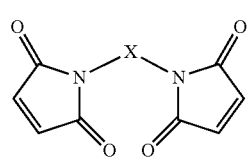

(I)

wherein X is a single bond, $C_1$-$C_{14}$ alkylene, polyethyleneglycol (PEG) or segments thereof, polypropylene glycol (PPG) or segments thereof, phenylene, methylenebis(phenylene), sulfonylbis(phenylene), oxybis(phenylene) and combinations thereof.

17. The crosslinked polymer according to claim 13, wherein the bismaleimide is selected from the group consisting of 1,1'-(Methylenedi-4,1-phenylene)bismaleimide (BM1), N,N'-hexamethylenebismaleimide, (BM2),N,N'-(1,4-Phenylene)dimaleimide (BM3) and N,N'-pentamethylenebismaleimide (BM4).

18. The crosslinked polymer according to claim 13, wherein the crosslinked polymer has one or more of the following characteristics: the crosslinks are removable at a temperature of more than 50° C., is devoid of an isocyanate group, easily recyclable, self-healing, thermo-healing and/or shape memory.

19. A coated substrate comprising:
a layer of crosslinked polyhydroxyurethane (PHU) polymer disposed over a surface of the substrate, the crosslinked PHU polymer comprising a plurality of diene-dienophile adducts, wherein at least a part of the diene-dienophile adduct comprises structure (I):

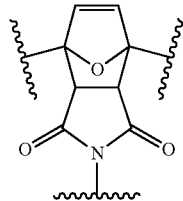

Structure (I)

wherein the crosslinked PHU polymer is obtained from reacting a crosslinking agent having two or more dienophile moieties with the PHU polymer backbone to form crosslinks between the diene moieties,
and optionally wherein the substrate is selected from the group consisting of wood, glass, metal, plastic and fabric and combinations thereof.

* * * * *